United States Patent
Inoue et al.

(10) Patent No.: US 9,110,087 B2
(45) Date of Patent: Aug. 18, 2015

(54) POLYMER FOR FILLER FOR PREPROCESSING COLUMN

(71) Applicants: Wako Pure Chemical Industries, Ltd., Osaka (JP); Nippon Filcon Co., Ltd., Tokyo (JP)

(72) Inventors: Yoshinori Inoue, Tokyo (JP); Kimiko Yoshida, Hyogo (JP); Mamoru Kubota, Hyogo (JP); Hitoshi Uemori, Hyogo (JP)

(73) Assignees: WAKO PURE CHEMICAL INDUSTRIES, LTD., Osaka (JP); NIPPON FILCON CO., LTD., Tokyo (JP)

( * ) Notice: Subject to any disclaimer, the term of this patent is extended or adjusted under 35 U.S.C. 154(b) by 124 days.

(21) Appl. No.: 13/950,013

(22) Filed: Jul. 24, 2013

(65) Prior Publication Data
US 2013/0309775 A1   Nov. 21, 2013

Related U.S. Application Data

(62) Division of application No. 13/058,844, filed as application No. PCT/JP2009/064128 on Aug. 10, 2009, now abandoned.

(30) Foreign Application Priority Data

Aug. 12, 2008  (JP) .................................. 2008-207879
Nov. 27, 2008  (JP) .................................. 2008-301822

(51) Int. Cl.
| | |
|---|---|
| C08F 236/20 | (2006.01) |
| G01N 30/96 | (2006.01) |
| C08F 236/22 | (2006.01) |
| C08F 224/00 | (2006.01) |
| B01J 41/14 | (2006.01) |
| B01J 41/20 | (2006.01) |
| C08F 8/30 | (2006.01) |
| C08F 8/32 | (2006.01) |
| C08F 220/32 | (2006.01) |
| C08F 220/36 | (2006.01) |
| G01N 30/02 | (2006.01) |

(52) U.S. Cl.
CPC ............... *G01N 30/96* (2013.01); *B01J 41/14* (2013.01); *B01J 41/20* (2013.01); *C08F 8/30* (2013.01); *C08F 8/32* (2013.01); *C08F 220/32* (2013.01); *C08F 220/36* (2013.01); *C08F 224/00* (2013.01); *C08F 236/20* (2013.01); *C08F 236/22* (2013.01); *B01J 2220/54* (2013.01); *G01N 30/02* (2013.01); *Y10T 436/141111* (2015.01); *Y10T 436/145555* (2015.01); *Y10T 436/147777* (2015.01); *Y10T 436/173845* (2015.01); *Y10T 436/182* (2015.01); *Y10T 436/193333* (2015.01); *Y10T 436/201666* (2015.01)

(58) Field of Classification Search
None
See application file for complete search history.

(56) References Cited

U.S. PATENT DOCUMENTS

| | | | |
|---|---|---|---|
| 2,630,429 A | 3/1953 | Hwa | |
| 4,340,483 A | 7/1982 | Lukas | |
| 4,419,490 A | 12/1983 | Bayer et al. | |
| 2001/0014461 A1* | 8/2001 | Hutchens et al. | ............ 435/7.92 |
| 2010/0029914 A1 | 2/2010 | Komiya | |

FOREIGN PATENT DOCUMENTS

| | | |
|---|---|---|
| JP | 53-90991 | 8/1978 |
| JP | 2002-517574 | 6/2002 |
| WO | 9964480 A1 | 12/1999 |
| WO | 2006132333 A1 | 12/2006 |

OTHER PUBLICATIONS

Yu, Journal of Chromatography A, 855 (1999) 129-136.*

(Continued)

*Primary Examiner* — Robert C Boyle
(74) *Attorney, Agent, or Firm* — Hamre, Schumann, Mueller & Larson, P.C.

(57) ABSTRACT

The present invention provides a polymer of the compound represented by formula [1]:

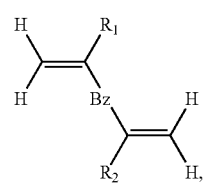

[1]

and the compound represented by formula [2]:

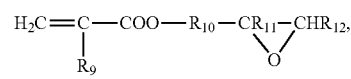

[2]

to a glycidyl group of which an anion exchanging group is introduced; a filler for measuring an acidic group binding to a perfluoro compound at a terminal, which comprises the polymer; a column filled with the filler; a method for measuring said perfluoro compound having an acidic group at a terminal by using the column; a filler or a column filled with the filler comprising the polymer for measuring a drug; and a method for measuring a drug by using the column.

19 Claims, No Drawings

(56) References Cited

OTHER PUBLICATIONS

Taniyasu et al., Analysis of fluorotelomer alcohols, fluorotelomer acids, and short- and long-chain perfluorinated acids in water and biota, J. of Chromatography A., 1093 (2005) 89-97.
Bisjak Chromotagraphia, 2005, 62, S31-S36.
Bilici Anaytica Chimica Acta (2004) 125-133.
Buchmeiser Polymer, 48, 2007, 2187-2198.
Li Journal of Polymer Science Part A: Polymer Chemistry, vol. 37, Issue 15, p. 2899-2907, published 1999.
Kuroda Die Angewandte Makromolekulare Chemie 237 (1996) 143-161.

* cited by examiner

POLYMER FOR FILLER FOR PREPROCESSING COLUMN

CROSS REFERENCE

This application claims the benefit of the following application: U.S. patent application Ser. No. 13/058,844 filed 11 Feb. 2011; the entire contents thereof are incorporated herein by reference.

TECHNICAL FIELD

The present invention relates to a novel polymer; a filler for measuring a perfluoro compound having an acidic group at terminal which comprises said polymer; a column filled with said filler; and a measuring method for a perfluoro compound having an acidic group at terminal by using said column; as well as a filler for measuring a drug which comprises the above-described polymer; a column filled with said filler; and a measuring method for a drug by using said column.

BACKGROUND ART

Perfluoro compounds having acidic groups at terminal such as perfluorooctane sulfonic acid (PFOS) and perfluorooctanoic acid (PFOA), which are perfluorinated fluorine compounds, have been widely used for various industrial products such as household articles, construction materials, semiconductors because of having excellent properties of heat resistance, chemical resistance, weathering resistance and the like. However, it has been recently found that such perfluoro compounds containing acidic group have remained in water of river, lake, seawater etc., and have been accumulating in the body of human and living organism because these compounds tend to migrate into water environment due to water-solubility, and are chemically very stable and persistent. Therefore, these compounds have been attracting the attention as the items to be monitored of the global environmental pollution, and the nationwide research on the environmental pollution by perfluoro compounds having acidic groups at terminal has been carried out. And as a micro-analytical method for perfluoro compound contained in the environmental water in this research, the method for analyzing the samples pretreated by using a solid-phase extraction column with LC/MS/MS and the like is employed. For example, the method for analyzing perfluoro compounds having acidic groups at terminal by using the solid-phase extraction method used with a processing column is described in non-patent reference 1 and the like. However, 10 to 20 kinds of perfluoro compounds having acidic groups at terminal are present depending on the difference of acidic groups at terminal and the number of carbon atoms thereof, and we have confirmed that all perfluoro compounds having acidic groups at terminal cannot be simultaneously analyzed by using the measuring method being carried out in the above-described reference. Therefore, the development of the method by which perfluoro compounds having acidic groups at terminal can be simultaneously and efficiently analyzed, has been desired.

On the other hand, need of the test of medicaments (drugs) contained in biological samples is recently increasing. In particular, doping test in the sports world needs to inspect various drugs, and needs to bring about no inspection mistake even when it is a trace amount. Usually, this drug test is carried out by solid-phase extracting with the preprocessing column, and further analyzing and detecting the obtained extraction liquid by using high-performance liquid chromatography or gas chromatography. However, since the above-described drug test is carried out by targeting the various drugs, the development of the preprocessing column which can adsorb any type of the basic, neutral, or acidic compounds, has been desired. On the other hand, patent reference 1 describes the porous resin compound having an ion-exchanging group, a hydrophobic component and a hydrophilic component as a column (filler) having such a wide adsorption target. However, even these compounds, they cannot efficiently adsorb all of the above-described target components. Therefore, further improvement has been needed.

PRIOR ART DOCUMENTS

Patent Documents

Patent Reference 1: JP-A-2002-517574;

Non-Patent Documents

NON-Patent Reference 1: Journal of Chromatography A, 19093 (2005)89-97;

SUMMARY OF INVENTION

Problem to be Solved by the Invention

Considering the above-described situation, the present inventors have extensively studied a way to attain the above-described object, and consequently, have found that a polymer obtained by introducing an anion-exchanging group into a glycidyl group in the polymer obtained by polymerization of the compound represented by the following general formula[1]:

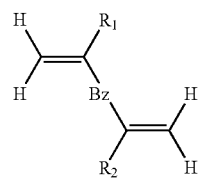

[1]

(wherein each of $R_1$ and $R_2$ independently represents a hydrogen atom, a linear alkyl group having 1 to 3 carbon atoms or a halogen atom, Bz represents benzene ring) and the compound represented by following general formula[2]:

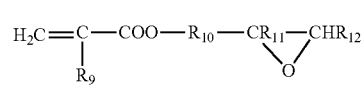

[2]

(wherein $R_9$ represents a hydrogen atom, a linear alkyl group having 1 to 3 carbon atoms or a halogen atom, $R_{10}$ represents a linear alkylene group having 1 to 3 carbon atoms, each of $R_{11}$ and $R_{12}$ independently represents a hydrogen atom, or a linear alkyl group having 1 to 6 carbon atoms) can become a filler for solving the above-described problems. Then, they have completed the present invention. That is, it has been found that the filler comprising said polymer can efficiently adsorb the various perfluoro compounds which have the acidic group at terminal (hereinafter, this compound may be abbreviated as the perfluoro compound having the acidic group), also, the filler comprising the above-described polymer can efficiently adsorb any one of the basic, neutral, or/and acidic compound. Thus, the present invention has been completed. It is a subject of the present invention to provide a novel polymer; a filler which can efficiently adsorb various acidic group binding perfluoro compound; and a measuring method for the perfluoro compounds having the acidic group by using said filler; as well as a filler which can efficiently adsorb the basic, neutral or/and acidic drugs; and a measuring method for the drugs by using said filler.

Means for Solving the Problems

The present invention relates to:

(1) a polymer obtained by introducing an anion exchanging group into a glycidyl group in the polymer obtained by polymerization of the compound represented by the following general formula [1]:

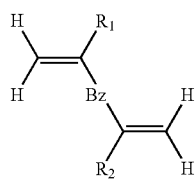

[1]

(wherein, each of $R_1$ and $R_2$ independently represents a hydrogen atom, a linear alkyl group having 1 to 3 carbon atoms or a halogen atom, Bz represents benzene ring) and the compound represented by the following general formula [2]:

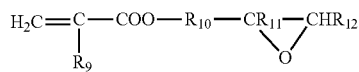

[2]

(wherein, $R_9$ represents a hydrogen atom, a linear alkyl group having 1 to 3 carbon atoms or a halogen atom, $R_{10}$ represents a linear alkylene group having 1 to 3 carbon atoms, each of $R_{11}$ and $R_{12}$ independently represents a hydrogen atom, or a linear alkyl group having 1 to 6 carbon atoms);

(2) a filler for measuring a perfluoro compound having an acidic group at terminal, comprising said polymer;

(3) a preprocessing column filled with said filler for measuring a perfluoro compound having an acidic group at terminal;

(4) a measuring method for a perfluoro compound having an acidic group at terminal characterized in using said column;

(5) a filler comprising the above-described polymer for measuring a drug;

(6) a preprocessing column filled with said filler for measuring a drug; and (7) a measuring method for a drug characterized in using said column.

Effect of the Invention

The filler comprising the polymer of the present invention can efficiently adsorb various perfluoro compounds having the acidic group. Therefore, by the method using said filler, particularly, by the measuring method in which solid-phase extraction is carried out by using said filler, it is possible to measure simultaneously and efficiently various perfluoro compounds having the acidic group. Further, by using LC/MS/MS as the separation measurement, it is possible to measure sensitively.

In addition, the filler comprising the polymer of the present invention can adsorb the target substances of the basic, neutral or/and acidic compound and the like equally or more efficiently comparing with the conventional filler for the preprocessing column having broad scope. Therefore, a plurality of targeting substances can be simultaneously and efficiently separated by concentration by means of one time pretreatment. Particularly, when drugs are provided as the target substances, the column is very useful as the preprocessing column for measuring the drugs because of capability of efficient adsorption. Furthermore, the adsorbed basic, neutral, or/and acidic compounds can be separately eluted as basic and neutral compounds and acidic compounds. Therefore, this method also gives the effect that separation analysis becomes easy for the many target substances.

MODES FOR CARRYING OUT THE INVENTION

Alkyl groups having 1 to 3 carbon atoms in $R_1$ and $R_2$ of the general formula [1] include, specifically, for example, a methyl group, an ethyl group, an n-propyl group and the like, and a methyl group is preferable.

Halogen atoms in $R_1$ and $R_2$ of the general formula [1] include a fluorine atom, a chlorine atom, a bromine atom, an iodine atom and the like.

The compounds represented by the general formula [1] include, specifically, for example,

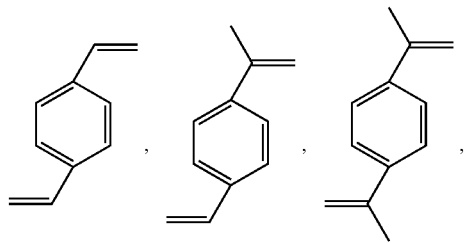

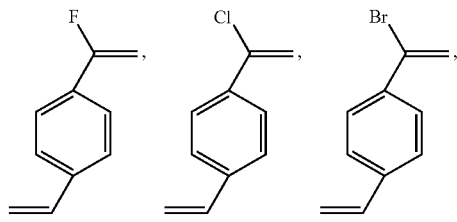

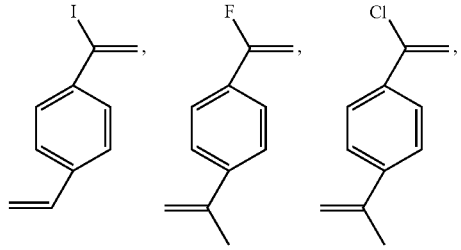

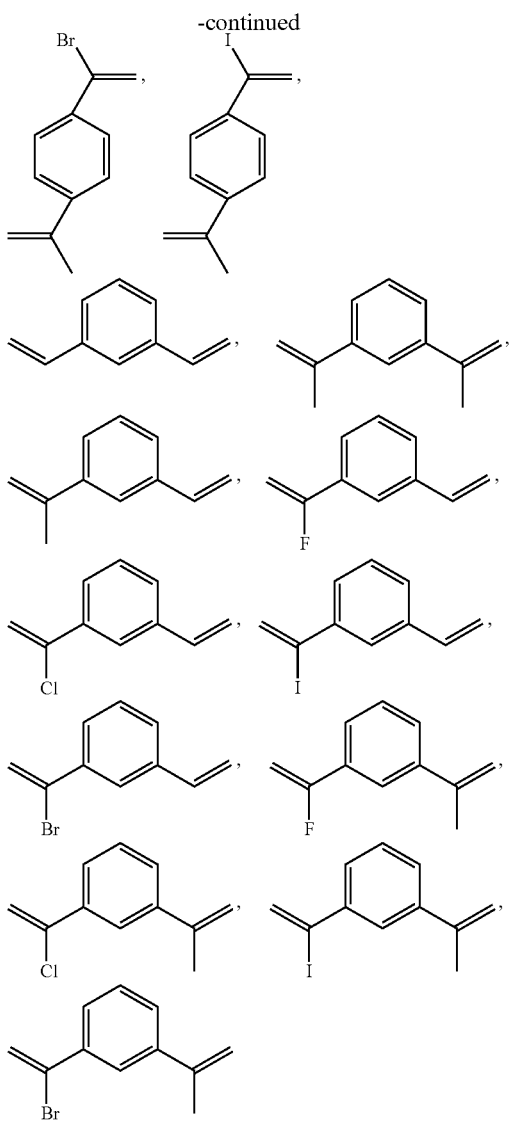

and the like.

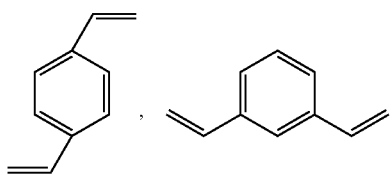

are preferable, and among them,

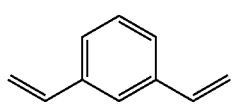

is particularly preferable.

Linear alkyl groups having 1 to 3 carbon atoms in $R_9$ of the general formula [2] include, specifically, for example, a methyl group, an ethyl group, an n-propyl group and the like, and a methyl group is preferable.

Halogen atoms in $R_9$ of the general formula [2] include a fluorine atom, a chlorine atom, a bromine atom, an iodine atom and the like.

Linear alkylene groups having 1 to 3 carbon atoms in $R_{10}$ of the general formula [2] include, for example, a methylene group, an ethylene group, an n-propylene group and the like, and a methylene group is preferable.

Linear alkyl groups having 1 to 6 carbon atoms in $R_{11}$ and $R_{12}$ of the general formula [2] include, for example, a methyl group, an ethyl group, an n-propyl group, an n-butyl group, an n-pentyl group, an n-hexyl group and the like. Among them, a methyl group is preferable.

Specific examples of the general formula [2] include, for example,

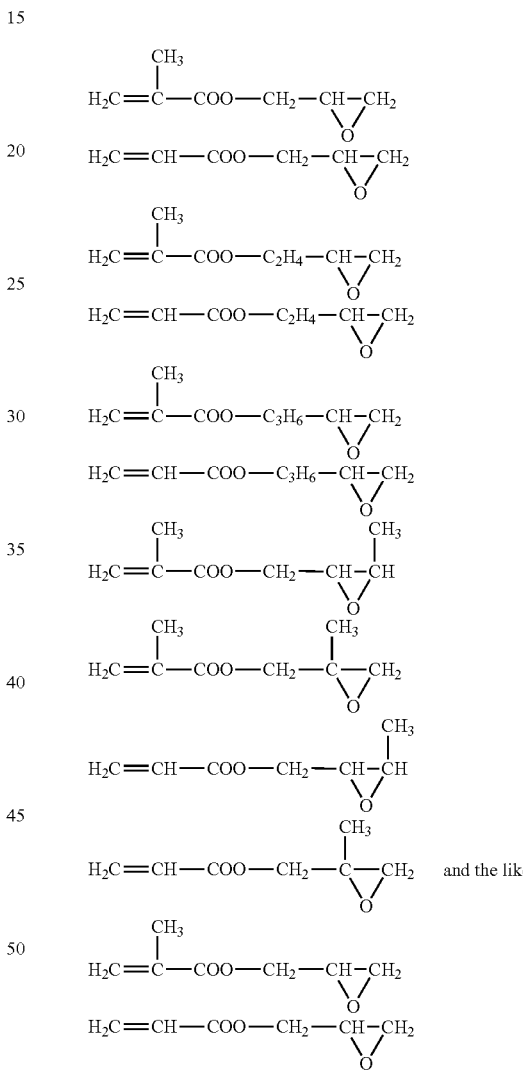 and the like.

and the like are preferable. Among them,

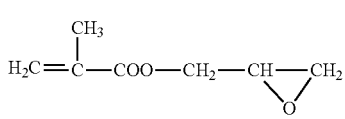

is particularly preferable.

Anion exchanging groups relevant to the present invention include, for example, a primary amino group, a secondary amino group, a tertiary amino group, a quaternary ammonium group and the like. Secondary amino groups include, for example, the group represented by —$NHR_{20}$ ($R_{20}$ represents an alkyl group which may contain an oxygen atom in the chain), and tertiary amino groups include the group represented by —$NHR_{21}R_{21'}$ (each of $R_{21}$, $R_{21'}$ independently represents an alkyl group which may contain oxygen atoms in the chain) or a cyclic amino group, and quaternary ammonium groups include the group represented by the following formula[3]:

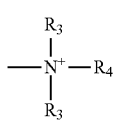

[3]

(wherein each of $R_3$ independently represents a linear alkyl group having 1 to 3 carbon atoms, and $R_4$ represents a linear alkyl group having 1 to 6 carbon atoms). As said anion exchanging group, a tertiary amino group is preferable when polymer is used as the filler for measuring the perfluoro compound having the acidic group, and a quaternary ammonium group is preferable when polymer is used as the filler for measuring the drugs.

Alkyl groups in the alkyl group which may have oxygen atoms represented by $R_{20}$ in the above-described secondary amino group may be linear, branched, or cyclic group, and a linear group is preferable. Alkyl groups include the group having normally 1 to 6 carbon atoms, preferably 1 to 4 carbon atoms, and more preferably 1 or 2 carbon atoms, and are specifically represented by, for example, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a neopentyl group, an n-hexyl group, an isohexyl group, a sec-hexyl group, a tert-hexyl group, an n-heptyl group, an isoheptyl group, a sec-heptyl group, a tert-heptyl group, an n-octyl group, a sec-octyl group, a tert-octyl group, a nonyl group, a decyl group, an undecyl group, a dodecyl group, a cyclopropyl group, a cyclopentyl group, a cyclohexyl group, a cycloheptyl group, a cyclooctyl group, a cyclononyl group, a cyclodecyl group, a cycloundecyl group, a cyclododecyl group and the like, and a methyl group and an ethyl group are preferable, and an ethyl group is more preferable. In addition, alkyl groups having oxygen atoms include the alkyl group having normally 1 to 5, preferably 1 to 2, more preferably 1 oxygen atom in the chain of the above-described alkyl group having 2 to 6 carbon atoms, and specific examples include, for example, —$CH_2$—O—$CH_3$, —$CH(CH_3)$—O—$CH_3$, —$CH_2$—$CH(CH_3)$—O—$CH_3$, —$CH_2CH_2$—O—$CH_2CH_2$, —$CH_2CH_2$—O—$C(CH_3)_3$, —$CH_2CH_2CH_2$—O—$CH_2CH_3$, —$CH_2CH_2CH_2$—O—$CH(CH_3)CH_3$, —$CH_2CH(CH_3)$—O—$CH_2CH(CH_3)CH_3$, —$CH_2$—O—$CH_2CH_2CH_2CH_2CH_2CH_3$, —$CH_2CH_2CH_2CH_2CH_2$—O—$CH_2$, —$CH_2CH_2$—O—$CH(CH_2CH_3)CH_2CH_3$, —$CH_2CH_2CH_2CH_2CH_2$—O—$CH_2CH_2CH_2CH_2CH_2CH_3$, —$CH_2CH_2CH_2CH_2$—O—$C(CH_3)_3$, —$CH_2CH_2CH_2$—O—$CH_2CH_2CH_2$—O—$CH_2CH_2CH_2$, —$CH_2CH_2CH_2CH_2CH_2CH_2CH_2CH_2CH_2CH_2$—O—$CH_2$, —$CH_2CH_2$—O—$CH_2CH_2$—O—$CH_2$—O—$CH_2CH_2$, —$CH_2CH_2$—O—$CH_2CH_2$—O—$CH_2$—O—$CH_2CH_2$—O—$CH_2CH_2CH_2$, —$CH_2CH_2$—O—$CH_2CH_2$— and —$CH_2CH_2$—O—$CH_2CH(CH_3)$ and the like.

Preferable specific examples of the above-described secondary amino group include, for example, a methylamino group, an ethylamino group, an n-propylamino group and the like.

Alkyl groups which may contain oxygen atoms represented by $R_{21}$, or $R_{21'}$ in the above-described tertiary amino group include the same as the alkyl groups which may contain oxygen atoms represented by the above-described $R_{20}$, and include, as preferable groups, a methyl group, an ethyl group and an n-propyl group, and among them, an ethyl group is preferable. It should be noted that, it is more preferable that both of $R_{21}$ and $R_{21'}$ are the same groups. Specific examples of tertiary amino groups represented by —$NR_{21}$ or $R_{21'}$ include, for example, a dimethylamino group, a diethylamino group, a methylethylamino group, a di-n-propylamino group, a diisopropylamino group, an 1-phenylethylamino group and the like, and among them, a diethylamino group is preferable.

Cyclic amino groups of tertiary amino group include an amino group constituting normally 3 to 12 membered ring, preferably 5 to 6 membered ring in cyclic part, specifically include, for example, the groups derived from membered rings such as an ethyleneimino group, for example, 5 membered rings such as a pyrrolidino group, imidazolino group, a pyrazolidino group, for example, 6 membered rings such as a piperidino group, a morpholino group, a piperazino group, for example, the groups derived from bicyclo rings such as a quinuclidino group, and among them, 6 membered rings such as a piperidino group, a morpholino group, a piperazino group are preferable, and further, a morpholino group is preferable.

Linear alkyl groups having 1 to 3 carbon atoms in $R_3$ of quaternary ammonium groups represented by the general formula [3] include, specifically, for example, a methyl group, an ethyl group, an n-propyl group and the like, and a methyl group is preferable.

Linear alkyl groups having 1 to 6 carbon atoms in $R_4$ of quaternary ammonium groups represented by the general formula [3] include, for example, a methyl group, an ethyl group, an n-propyl group, an n-butyl group, an n-pentyl group, an n-hexyl group and the like, and among them, a methyl group is preferable.

Ammonium groups represented by the general formula [3] include, specifically, for example, a trimethylammonium group, an ethyldimethylammonium group, a dimethyl-n-propylammonium group, an n-butyldimethylammonium group, a dimethyl-n-pentylammonium group, a dimethyl-n-hexylammonium group, a diethylmethylammonium group, a triethylammonium group, a tri-n-ammonium group and the like, and among them, a trimethylammonium group, an ethyldimethylammonium group are preferable, and an ethyldimethylammonium group is particularly preferable.

Linear alkylene groups having 1 to 3 carbon atoms in $R_{15}$ of the general formula [4] include, for example, a methylene group, an ethylene group, an n-propylene group and the like, and a methylene group is preferable.

Linear alkyl groups having 1 to 3 carbon atoms in $R_{16}$ of the general formula [4] include, for example, a methyl group, an ethyl group, an n-propyl group and the like, and a methyl group is preferable. In addition, halogen atoms in $R_{16}$ include a fluorine atom, a chlorine atom, a bromine atom, an iodine atom and the like.

Compounds represented by the general formula [4] include, specifically, for example,

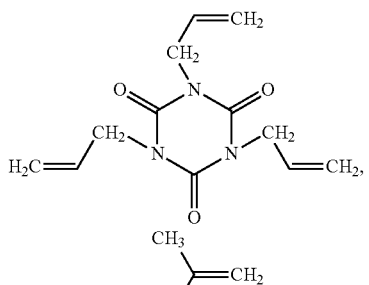

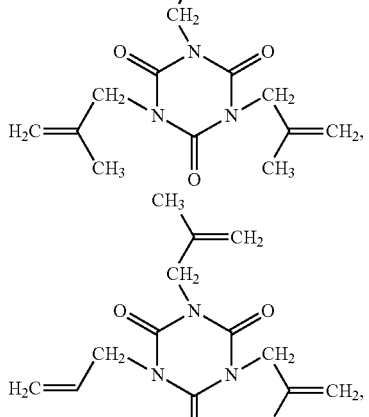

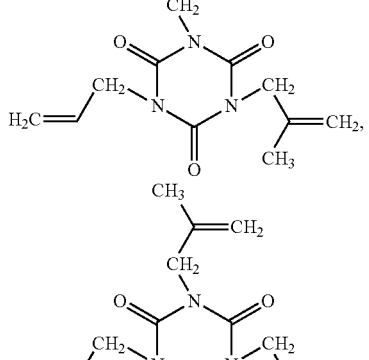

and the like, and among them,

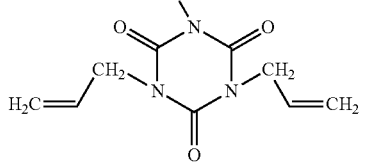

is preferable.

The polymers obtained by introducing the anion exchanging group into glycidyl group of the polymer (hereinafter, this polymer may be abbreviated as the polymer of the present invention) obtained by polymerization of the compound represented by the general formula [1] and the compound represented by the general formula [2] (hereinafter, this polymer may be abbreviated as the prepolymer relevant to the present invention) include, for example, the following general formula [5]:

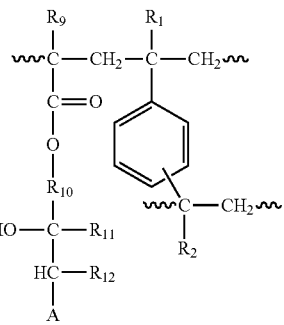
[5]

(wherein $R_1$, $R_2$, $R_9$, $R_{10}$, $R_{11}$ and $R_{12}$ are as above-described. A represents the anion exchanging group relevant to the present invention), specifically, for example,

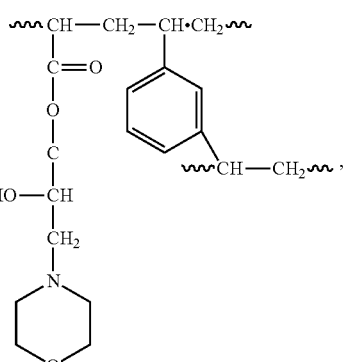

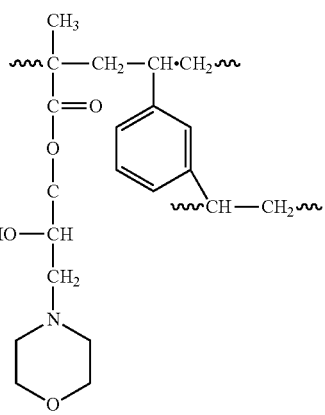

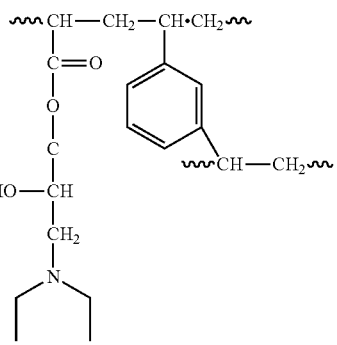

11
-continued
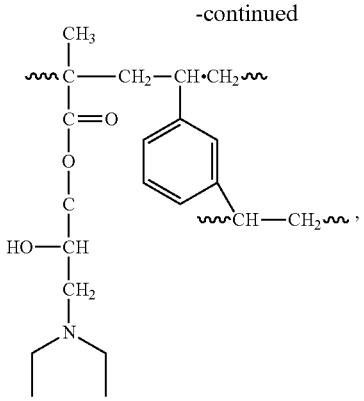
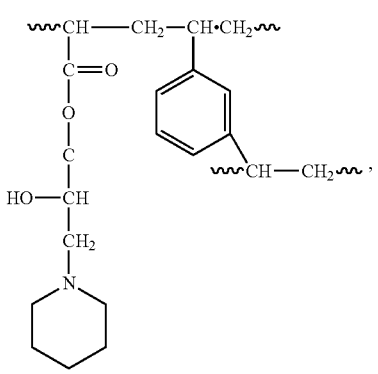
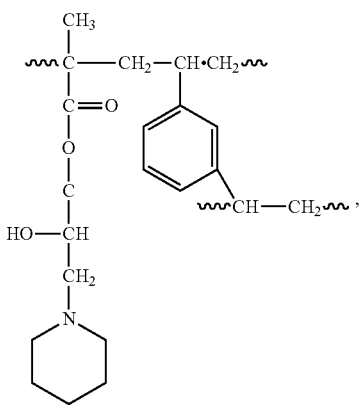
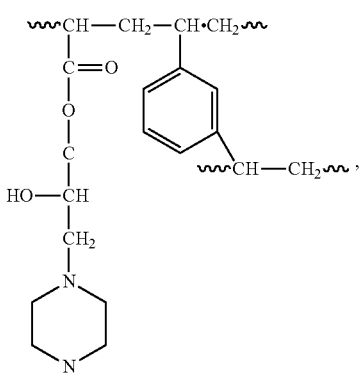
12
-continued
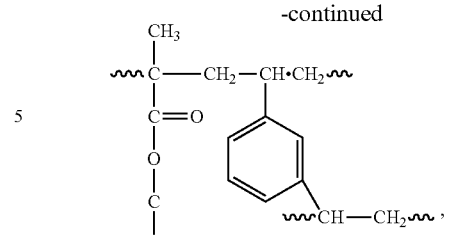
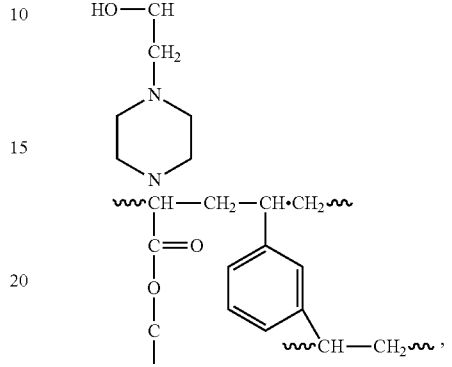
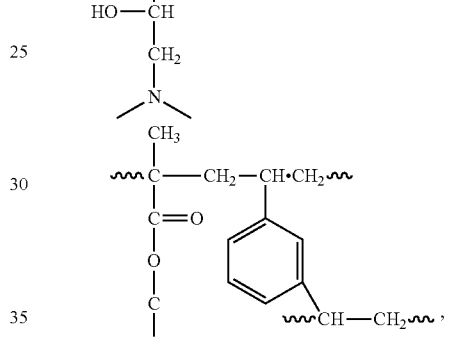
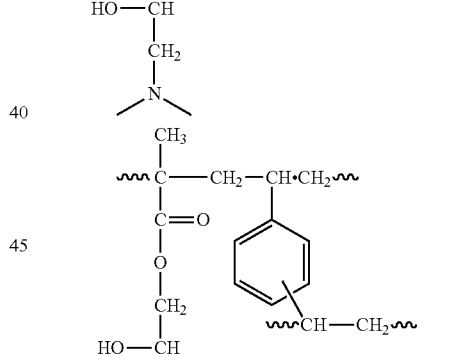
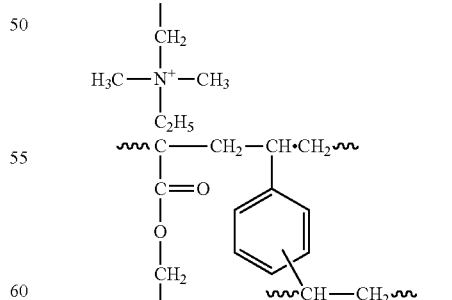
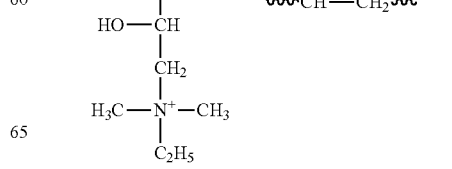

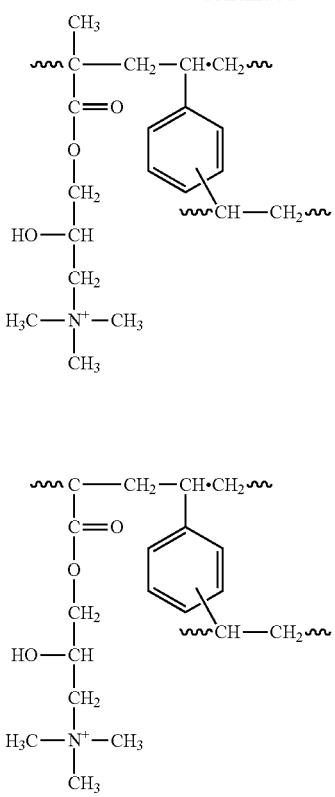
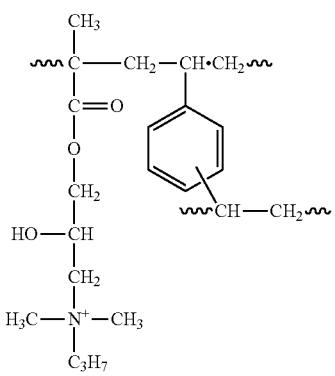
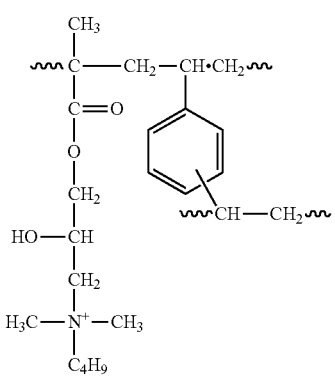
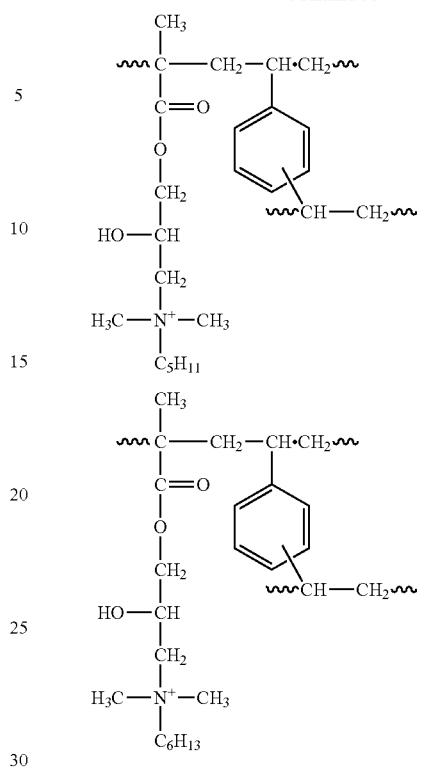
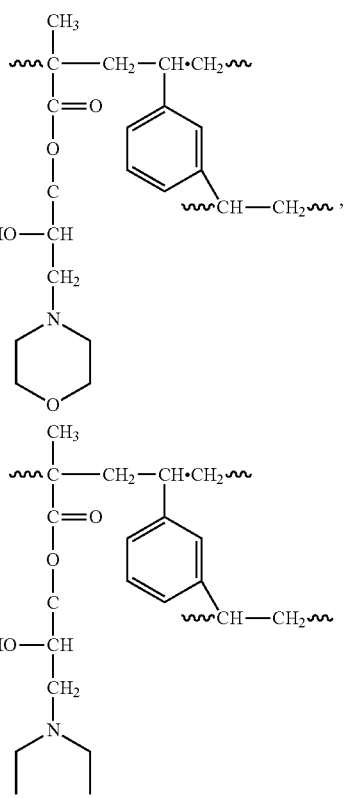
and the like. When the polymer is used as the filler for measuring the perfluoro compound having the acidic group, and the like are preferable. When the polymer is used as the filler for measuring drugs,

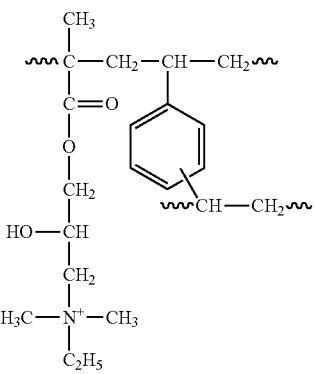

and the like are preferable.

In addition, the polymers of the present invention also include the polymer obtained by introducing an ammonium group represented by the general formula [3] into a glycidyl group of the polymer obtained by polymerization of the monomers containing the compound represented by the general formula [1] and the compound represented by the general formula [2], and further the compound represented by the general formula [4], and are specifically represented by, for example, the following general formula [6]:

[6]

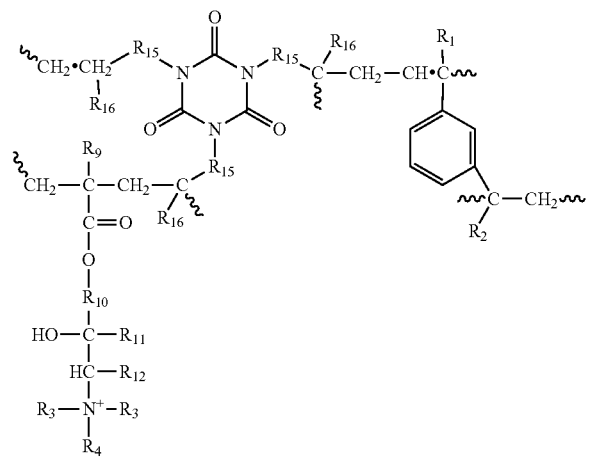

(wherein $R_1$, $R_2$, $R_3$, $R_4$, $R_9$, $R_{10}$, $R_{11}$, $R_{12}$, $R_{15}$ and $R_{16}$ are as above-described). Said polymer is preferable for the filler for measuring the drug. Specific examples of said general formula [6] are, for example,

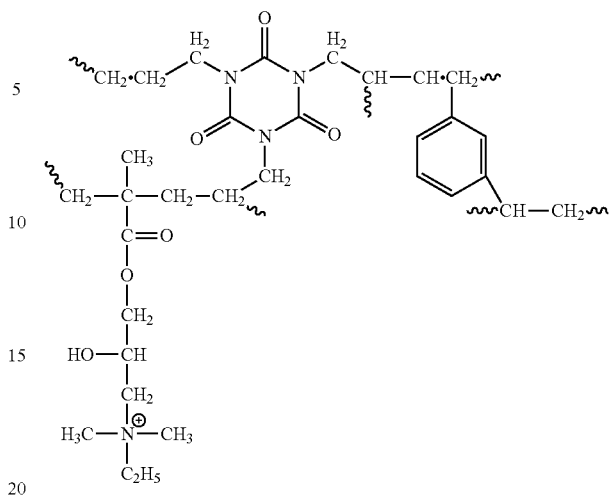

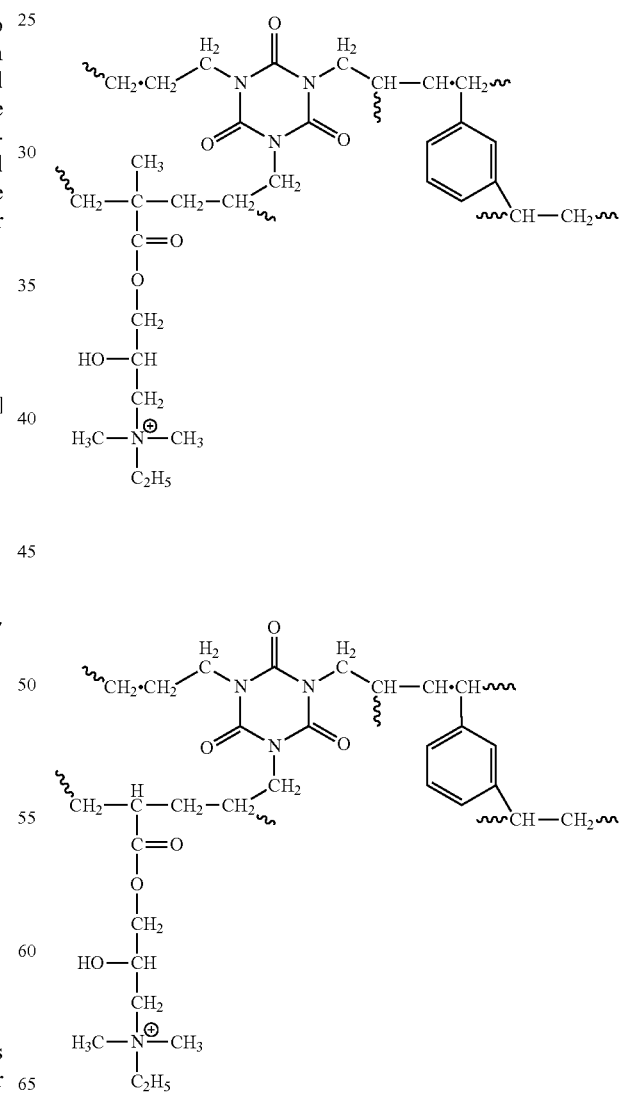

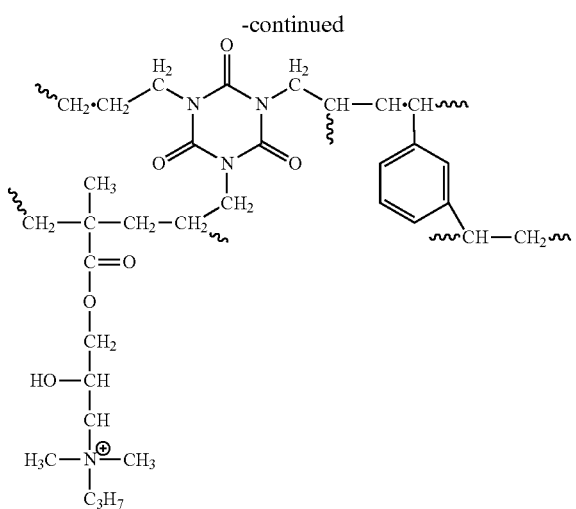

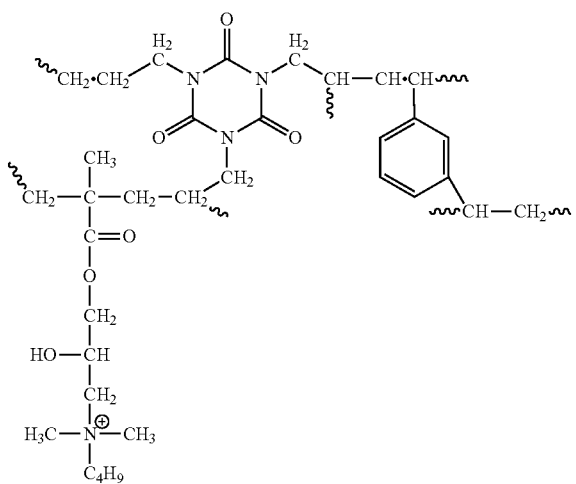

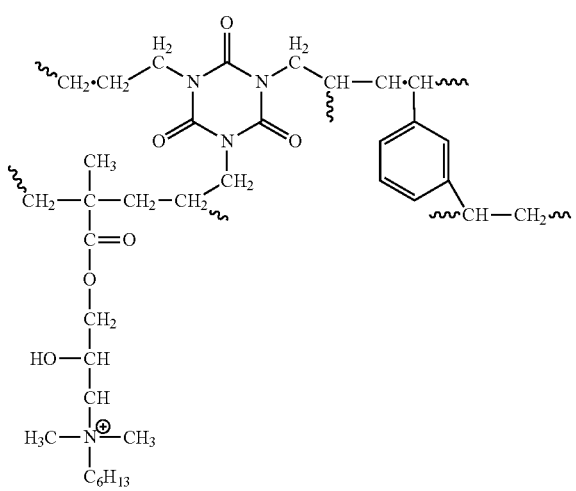

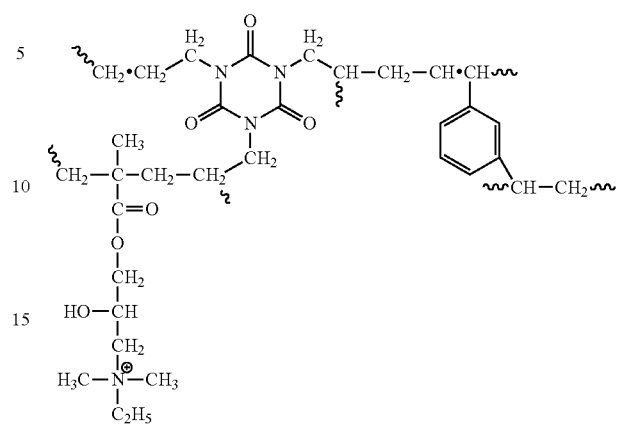

and the like, and among them, is preferable.

Average particle diameter of the polymer of the present invention is normally 10 to 100 μm, preferably 20 to 100 μm, more preferably 30 to 70 μm, and micropore diameter is normally 3 to 15 nm. When polymer is used as the filler for measuring the perfluoro compound having the acidic group, 10 to 15 nm is preferable. When the polymer is used as the filler for measuring the drugs, 3 to 5 nm is preferable. Specific surface area of the polymer is normally 200 to 1000 $m^2/g$, preferably 300 to 700 $m^2/g$. When polymer is used as the filler for measuring the perfluoro compound having the acidic group, 600 to 700 $m^2/g$ is particularly preferable. When polymer is used as the filler for measuring drugs, 300 to 500 $m^2/g$ is particularly preferable. When the polymer of the present invention is synthesized from the monomers containing the compound represented by the general formula [1] and the compound represented by the general formula [2], molar ratio of the compound represented by the general formula [1] and the compound represented by the general formula [2] is normally 60 to 90:10 to 40, preferable range is 70 to 85:15 to 30. In addition, when the polymer of the present invention is synthesized from the monomers containing the compound represented by the general formula [1], the compound represented by the general formula [2] and the compound represented by the general formula [4], molar ratio of the compound represented by the general formula [1], the compound represented by the general formula [2] and the compound represented by the general formula [4] is normally 60 to 85:14 to 30:1 to 10, preferable range is 70 to 80:18 to 25:2 to 5. The polymer of the present invention is the one in which anion exchanging group is contained normally 0.1 to 1.0 mmol in 1 g of said polymer, preferable range is 0.2 to 0.6 mmol.

Synthetic method of the present invention may be carried out by polymerizing the monomers containing the compound represented by the general formula [1] and the compound represented by the general formula [2], or the monomers (hereinafter, these monomers may be abbreviated as the monomer group relevant to the present invention) containing the compound represented by the general formula [1] and the compound represented by the general formula [2] and the compound represented by the general formula [4] by the known polymerization method, and by introducing the anion exchanging group into glycidyl group at terminal of the obtained polymer (hereinafter, the polymer may be abbreviated as prepolymer relevant to the present invention) by the known method (for example, amination reaction and the like).

Specifically, for example, after the monomer group relevant to the present invention and polymerization initiator are dissolved in the organic solvent which can dissolve these monomer group and polymerization initiator but is insoluble in water, suspension polymerization is carried out in the water by adding said organic solvent to water, and then, the prepolymer relevant to the present invention is obtained. When the monomers having the compound represented by the general formula [1] and the compound represented by the general formula [2] are used as the monomer group relevant to the present invention, molar ratio of the compound represented by the general formula [1] and the compound represented by the general formula [2] is normally 60 to 90:10 to 40, preferable range is 70 to 85:15 to 30. In addition, when the monomers containing the compound represented by the general formula [1] and the compound represented by the general formula [2] and the compound represented by the general formula [4] are used as the monomer group relevant to the present invention, molar ratio of the compound represented by the general formula [1] and the compound represented by the general formula [2] and the compound represented by the general formula [4] is normally 60 to 85:14 to 30:1 to 10, preferable range is to 80:18 to 25:2 to 5. As a polymerization initiator, any one can be used as long as it is well-known itself, and includes, for example, azoisobutyronitrile, 2,2'-azobis(2, 4-dimethylvaleronitrile), 2,2'-azobis(methyl 2-methylpropionate), 2,2'-azobis(2-methylbutyronitrile), benzoyl peroxide, lauroyl peroxide and the like. Amount of use of the polymerization initiator is 0.1 to 3% by weight relative to total weight of the monomer group relevant to the present invention. In addition, organic solvents to be used here include, for example, toluene, ethylbenzene, butyl acetate, amyl acetate, octylalcohol, dodecylalcohol, octane, dodecane and the like. Amount of use of the solvent is 0.5 to 2 times weight of total weight of monomers relevant to the present invention. Amount of water to be used here is normally 1 to 10 times weight relative to sum of the weight of monomer group relevant to the present invention and the weight of the above-described organic solvent. In addition, aqueous organic polymer such as polyvinyl alcohol and methylcellulose as a suspension stabilizer known in itself are preferably dissolved in said water, and amount of stabilizer is normally 0.01 to 1% by weight in the water. Suspension polymerization reaction is carried out normally at 60 to 90° C., for 4 to 20 hours. After the reaction, the prepolymer relevant to the present invention can be obtained by treating according to common procedure of obtaining the polymer. The obtained prepolymer relevant to the present invention is preferably classified by using sieves in order to obtain the prepolymer having the particle diameter suitable for filler, and also, to obtain the prepolymer having uniform largeness for performing the excellent capability of adsorption. Particle diameter of the prepolymer relevant to the present invention obtained by sieve classification is normally 10 to 100 μm, preferable range is 20 to 100 μm, more preferable range is 30 to 70 μm. In addition, operation of said classification may be carried out after obtaining the polymer of the present invention.

Subsequently, the obtained prepolymer relevant to the present invention is suspended or swelled in suitable organic solvent or the mixed aqueous solution of said organic solvent and water, and the compound which contains the anion exchanging group (the anion exchanging group containing compound) is added to said solution to perform amination reaction, and thus, the polymer of the present invention can be obtained. The above-described organic solvents include 1,4-dioxane, tetrahydrofuran, isopropanol, N,N-dimethylformamide, dimethylsulfoxide and the like. When mixed aqueous solution of organic solvent and water is used, amount of water is normally 10 to 60% as an amount in the mixed aqueous solution, and preferable range is 20 to 50%. The amount of the above-described organic solvent or mixed aqueous solution of organic solvent and water is 1 to 10 times weight relative to the weight of the prepolymer relevant to the present invention. If the anion exchanging group containing compound is the one which contains the above-described anion exchanging group, and by which the desired polymer can be obtained, it is not particularly limited thereto. For example, and the polymer in which hydrogen atom or methyl group and the like is bounded to terminal of the above-described anion exchanging group is exemplified, and amount of use of the polymer is normally 0.001 to 0.05 mole relative to 1 kg of prepolymer relevant to the present invention, preferable range is 0.002 to 0.025 mole. Amination reaction is carried out at room temperature to 60° C., normally for 4 to 30 hours, preferably for 10 to 20 hours, while stirring if necessary. The polymer of the present invention is obtained by this reaction.

The case of employing divinylbenzene as a compound represented by the general formula [1], glycidyl methacrylate as a compound represented by the general formula [2], and diethylamine as the anion exchanging group containing compound, is taken for an example, and the synthetic method of the polymer of the present invention is described below. It should be noted that, said polymer is preferable as the filler for measuring the perfluoro compound having the acidic group.

That is, for example, in 100 g of organic solvent such as toluene, 75 to 90 g of divinylbenzene (0.2 to 0.6 mol as an amount of pure divinylbenzene), and 10 to 25 g of glycidyl methacrylate (0.05 to 0.2 mol) and 1 to 3 g of polymerization initiator such as azobisisobutyronitrile are mixed, the resultant organic solvent is suspended in 500 to 1000 mL of 0.01 to 1.0% by weight of methyl cellulose aqueous solution, and is reacted at 60 to 80° C. for 5 to 10 hours. It should be noted that, when divinyl benzene is employed, there exists divinyl benzene containing impurities such as ethylvinylbenzene in commercially available divinylbenzene, however, in the present invention, the divinylbenzene containing such impurities may be provided to synthetic reaction as it is. In that case, although the content of divinylbenzene is reduced, the divinylbenzene can be used even when molar ratio to the other compounds is within the range defined in the section of the above-described polymer of the present inventions. Hereinafter, use of divinylbenzene is the same as above. By this method, the prepolymer relevant to the present invention can be obtained. After the reaction, the resultant polymer is washed with water or methanol if necessary. Subsequently, 10 g of prepolymer relevant to the present invention is suspended in 50 to 100 mL of 20 to 50% by volume of 2-propanol aqueous solution, and 10 to 50 g of diethylamine (0.1 to 0.5 mol) is added, and further the reaction solution is reacted at 40 to 60° C. for 10 to 20 hours while stirring, and then, the polymer of the present invention can be obtained.

The case of employing divinylbenzene as a compound represented by the general formula [1], glycidyl methacrylate as a compound represented by the general formula [2], and N,N-dimethylaminoethane as the anion exchanging group containing compound is taken for an example, and synthetic method of the polymer of the present invention is described below. It should be noted that, said polymer is preferable as the filler for measuring the drugs.

That is, for example, in 100 g of organic solvent such as toluene, 75 to 90 g of divinylbenzene (0.2 to 0.6 mol as an amount of pure divinylbenzene), and 10 to 25 g of glycidyl methacrylate (0.05 to 0.2 mol) and 1 to 3 g of polymerization initiator such as azobisisobutyronitrile are mixed, and the resultant organic solvent is suspended in 500 to 1000 mL of 0.01 to 1.0% by weight of methyl cellulose aqueous solution, and is reacted at 60 to 80° C. for 5 to 10 hours. By this method, the prepolymer relevant to the present invention can be obtained. After the reaction, the resultant polymer relevant to the present invention is washed with water or methanol if necessary. Subsequently, 10 g of prepolymer relevant to the present invention is suspended in 50 to 100 mL of 20 to 50% by volume of 2-propanol aqueous solution, 10 to 50 g of N,N-dimethylaminoethane (0.1 to 0.5 mol) is added, and the organic solution is reacted at 40 to 60° C. for 10 to 20 hours while stirring. Then, the polymer of the present invention can be obtained.

The case of employing divinylbenzene as a compound represented by the general formula [1], glycidyl methacrylate as a compound represented by the general formula [2], triallyl isocyanurate as a compound represented by the general formula [4], and N,N-dimethylaminoethane as the anion exchanging group containing compound is taken for an example, and synthetic method of the polymer of the present invention is described below. It should be noted that, said polymer is preferable as the filler for measuring the drugs.

That is, for example, in 100 g of organic solvent such as toluene, 85 to 70 g of divinylbenzene (0.2 to 0.6 mol as an amount of pure divinylbenzene), and 10 to 20 g of glycidyl methacrylate (0.05 to 0.2 mol) and 5 to 10 g of triallyl isocyanurate (0.02 to 0.04 mol), 1 to 3 g of polymerization initiator such as azobisisobutyronitrile are mixed, and the resultant organic solvent is suspended in 500 to 1000 mL of 0.01 to 1.0% by weight of methyl cellulose aqueous solution, and is reacted at 60 to 80° C. for 5 to 10 hours. By this method, the prepolymer relevant to the present invention can be obtained. After the reaction, the resultant polymer relevant to the present invention is washed with water or methanol if necessary. Subsequently, 10 g of prepolymer relevant to the present invention is suspended in 50 to 100 mL of 20 to 50% by volume of 2-propanol aqueous solution, and 10 to 50 g of N,N-dimethylaminoethane (0.1 to 0.5 mol) is added, and the organic solution is reacted at 40 to 60° C. for 10 to 20 hours while stirring. Then, the polymer of the present invention can be obtained.

The acidic groups of the perfluoro compound having the acidic group relevant to the present invention include sulfo group, carboxyl group, hydroxyl group and the like, and sulfo group, carboxyl group are preferable. The perfluoro compounds having sulfo group at terminal include the ones having 2 to 18 carbon atoms and the like, preferably 4 to 10 and the like. The perfluoro compounds having carboxyl group at terminal include the ones having 2 to 18 carbon atoms and the like, preferably 4 to 18, more preferably 4 to 12, further preferably 4 to 10 and the like. The perfluoro compounds having hydroxy group at terminal include the ones having 2 to 18 carbon atoms and the like, preferably 4 to 10 and the like. It should be noted that, the perfluoro compounds having the acidic group relevant to the present invention also include the ones which can form salts by substituting hydrogen ion of sulfo group or carboxyl group at terminal of the above-described perfluoro compounds having the acidic group with sodium ion, potassium ion or ammonium ion. Preferable specific examples include, for example, perfluoro sulfonic acids such as perfluoro butane sulfonic acid ($C_4F_9$—$SO_3H$, abbreviation: PFBS), perfluoro hexane sulfonic acid ($C_6F_{13}$—$SO_3H$, abbreviation: PFHxS), perfluoro octane sulfonic acid ($C_9F_{17}$—$SO_3H$, abbreviation: PFOS), perfluoro decane sulfonic acid ($C_{10}F_{21}$—$SO_3H$, abbreviation: PFDS); perfluoro carboxylic acids such as perfluoro butanoic acid ($C_4F_9$—COOH, abbreviation: PFBA), perfluoro pentanoic acid ($C_5F_{11}$—COOH, abbreviation: PFPeA), perfluoro hexanoic acid ($C_6F_{13}$—COOH, abbreviation: PFHxA), perfluoro heptanoic acid ($C_7F_{15}$—COOH, abbreviation: PFHpA), perfluoro octanoic acid ($C_9F_{17}$—COOH, abbreviation: PFOA), perfluoro nonanoic acid ($C_9F_{19}$—COOH, abbreviation: PFNA), perfluoro decanoic acid ($C_{10}F_{21}$—COOH, abbreviation: PFDA), perfluoro undecanoic acid ($C_{11}F_{23}$—COOH, abbreviation: PFUnDA), perfluoro dodecanoic acid ($C_{12}F_{25}$—COOH, abbreviation: PFDoDA), perfluoro tetradecanoic acid ($C_{14}F_{29}$—COOH, abbreviation: PFTeDA), perfluoro hexadecanoic acid ($C_{16}F_{33}$—COOH, abbreviation: PFHexDA), perfluoro octadecanoic acid ($C_{18}F_{37}$—COOH, abbreviation: PFODA).

The filler for measuring the perfluoro compound having the acidic group of the present invention is the one containing the polymer of the present invention obtained as described above.

The preprocessing column for measuring the perfluoro compound having the acidic group (hereinafter, this may be abbreviated as the preprocessing column for PF of the present invention) is the one filled with the above-described filler for measuring the perfluoro compound having the acidic group of the present invention. Filling method and the like is not particularly limited, and, in the column container normally used in this field, the above-described filler may be filled according to the known method, for example, slurry method, dry type-tapping method and the like. Amount of the filler may be determined according to the amount of use of the sample, for example, when 1000 ml of samples of environmental water such as river water, lake water, sea water; tap water, well water, spring water, body fluid and the like are passed through column to adsorb the perfluoro compound having the acidic group, amount of the filler is normally 10 to 1000 mg, preferably 50 to 250 mg. Column volume may be appropriately selected according to the filling material.

The measuring method of the perfluoro compound having the acidic group using the preprocessing column for PF of the present invention may be carried out by the following steps:

(1) a step of passing the sample containing the perfluoro compound having the acidic group through the preprocessing column for PF of the present invention to adsorb the perfluoro compound having the acidic group;

(2) a step of eluting the perfluoro compound having the acidic group by eluate; and (3) a step of measuring the obtained perfluoro compound having the acidic group.

In addition, in case of the sample having much impurities such as river water, lake water, the preprocessing column for PF of the present invention may be washed after adsorbing the perfluoro compound having the acidic group in order to remove these impurities from the preprocessing column for PF of the present invention.

Detail of the measuring method of the perfluoro compound having the acidic group using the preprocessing column of the present invention is specifically described as bellows. That is, first, (1) when the sample containing the perfluoro compound having the acidic group is passed through the preprocessing column for PF of the present invention to adsorb the perfluoro compound having the acidic group onto the column (filler), method of passing the liquid may be free fall, or may be carried out by pressurization or depressurization, and, pressurization or depressurization method is preferable. When pressurization or depressurization method is employed, adsorption rates are decreased when flow rates of sample become too high, and therefore, flow rates of sample are determined normally at to 30 mL/min, preferably at 10 to 30 mL/min, more preferably at 10 to 20 mL/min. In addition, it is considered that the perfluoro compound having the acidic group is held by ion exchange capacity of the anion exchanging group in the polymer used as the filler of the present invention, and therefore, when the sample has basicity such as pH 8 or more, it is preferable to pass the liquid after adjusting pH to 7 or less by the known neutralization reaction. When washing is carried out after operation of (1), washing solution may be passed through column, and said washing solutions include aqueous organic solvents having pH 8 or less, such as methanol, ethanol, propanol, acetonitrile, acetone. The amount of the solvent may be appropriately determined according to the amount of the filler, and it is normally 0.5 to 10 mL, preferably 0.5 to 5 mL relative to 10 mg of filler. Adjustment of pH is not particularly limited if it is carried out by using the acidic compounds used normally in this field, and the acidic compounds include, preferably, for example, hydrochloric acid, nitric acid, sulfuric acid and the like. Method of passing the liquid may be free fall, or may be carried out by pressurization or depressurization, and, pressurization or depressurization method is preferable because the washing solution can be removed perfectly. Next, (2) when the perfluoro compound having the acidic group adsorbed onto the preprocessing column for PF of the present invention are eluted by eluate, the eluates include a buffer solution having pH 8 to pH 14, preferably 9 to 14, a basic aqueous solution, an aqueous organic solvent such as methanol, ethanol, propanol, acetonitrile, acetone, and a mixed aqueous solution of said aqueous organic solution and basic aqueous solution or buffer solution, and the like since it is considered that the perfluoro compound having the acidic group is held by ion exchange capacity of the anion exchanging group in the polymer used as the filler of the present invention. Adjustment of pH is not particularly limited as long as it is carried out by using the basic compounds normally to be used in this field, and the basic compounds include, preferably, for example, ammonia. When ammonia is used, concentration of ammonia is normally 0.1 to 2 w/w % by weight, preferably 0.1 to 1 w/w % as concentration in eluate. In addition, amount of use of eluate may be appropriately determined according to the amount of the filler, and may be normally 0.3 to 100 mL, preferably 0.3 to 10 mL, more preferably 0.3 to 1 mL relative to 10 mg of the filler. Further, (3) By measuring the eluate containing the eluted perfluoro compound having the acidic group with the known separation measurement method, amount or concentration of the perfluoro compound having the acidic group in the sample can be obtained. If necessary, after the eluate containing the perfluoro compound having the acidic group which is used for separation measurement, is condensed by the known method, the elute may be provided with the separation measurement method. The separation measurement methods include, for example, liquid chromatography method, electrophoretic method and the like. UV detection, fluorescence detection, MS, MS/MS, evaporative light scattering detection (ELSD) and the like known in itself may be used as the detection tool, and measurement condition and the like may be determined according to the one which is normally employed in this field. Among said separation measurement methods, LC/MS/MS is preferable considering from the point of separation and sensibility.

More specifically, for example, the measuring method is carried out as follows. That is, for example, when 1000 mL of the sample having 0.1 ng to 1 mg/1 L, preferably 0.1 ng to 1 µg/1 L, more preferably 0.1 to 100 ng/1 L of perfluoro compound having the acidic group is used, the column filled with normally 10 to 1000 mg, preferably 50 to 200 mg of the filler of the present invention for measuring the perfluoro compound having the acidic group is used, and the sample is passed through said column by pressuring or depressuring at flow rates of 5 to 20 ml/min. Subsequently, the column is washed by passing 5 to 10 mL of purified water having pH 6 to 8 at flow rates of 5 to 10 mL/min, using pressuring or depressuring method. Next, by using 2 to 6 mL of methanol having 0.1 to 1% of ammonia, it is eluted by free fall. By measuring the obtained eluate with LC/MS/MS, under the condition which is normally employed in this field, the perfluoro compounds having the acidic group in the sample can be measured.

The drugs relevant to the present invention include all the materials having medicinal properties, and the doping substance such as diuretic and the other concealment drug, stimulant drug, narcotic, β-blocker, specific material listed in The 2008 Prohibited List International Standard (World Anti-Doping Code), 2008 Monitoring Program and the like, and the medicament or drug, which can temporally heighten or lessen the racing performance of race-horse, described in the Attached Table (2) in Ordinance for Enforcement of Horse Racing of The Japan Racing Association of the Japan Racing Association Rule No. 2 effective in Heisei 19 year (2007). Among them, the medicament or drug, which can temporally heighten or lessen the racing performance of race-horse, are preferable, specifically, for example, Atoropine, Amobarbital, Allobarbital, Antipyrine, Oxyethyltheophylline, Oxypropyltheophylline, 3'-Oxohexobarbital, Caffeine, Chlorpromazine, Cocaine, Cyclobarbital, β,γ-Dihydroxydibucaine, Dibucaine, Cyproheptadine, Cyproheptadine-N-oxide, Dimorphoramine, Scopolamine, Strychnine, Secobarbital, Theophylline, Tetracaine, Nikethamide, Nicotine, Noscapine, Barbital, 3'-Hydroxyamobarbital, γ-Hydroxydimorphoramine, 3'-Hydroxysecobarbital, 3'-Hydroxyhexobarbital, 3'-Hydroxypentobarbital, Pipradrol, Phenacetin, Phenylethylmalondiamide, Phenylbutazone, Phenobarbital, Primidone, Brucaine, Procaine, Promazine, Hexobarbital, Pentazocine, Pentetrazol, Pentobarbital, Methapyrilene, Methamphetamine, Metharbital, Methylephedrine, Methylphenidate, Methoxyphenamine, Mephobarbital, Monoethylglycinexylidide, Lidocaine, Chlorpromazine sulfoxide, Nortriptylin, Salicylic acid, Naproxen, and the like. Among them, Theophylline, Scopolamine, Caffeine, Atoropine, Barbital, Nortriptylin, Salicylic acid, Naproxen and the like are preferable.

The filler for measuring the drug of the present invention is the one containing the polymer of the present invention obtained as described above.

The preprocessing column for measuring the drugs of the present invention is the one filled with the above-described filler for measuring the drug of the present invention. Filling method and the like is not particularly limited, the above-described filler may be filled into the column container conventionally used in this field, according to the known method, for example, slurry method, dry type-tapping method and the like. The amount of filler in the column may be determined according to the amount of sample to be used, for example, when 10 mL of the sample having 0.001 to 50 µg/mL, preferably 0.05 to 10 µg/mL of drug is passed through column to adsorb the drug, the amount of the sample is normally 10 to 1000 mg, preferably 50 to 200 mg, more preferably 50 to 100 mg. Column volume may be appropriately selected according to the amount of filler.

Measuring method of the drugs using the preprocessing column for measuring the drugs of the present invention may be carried out by the following steps:

(1) a step of passing the sample containing the drugs through the preprocessing column for measuring drugs of the present invention to adsorb the drugs;

(2) a step of eluting the drugs by eluate; and (3) a step of measuring the eluted drugs.

In addition, in case of the sample having much impurities, treatment such as washing may be carried out after adsorbing the drugs in order to remove these impurities from the preprocessing column for measuring the drugs of the present invention.

Detail of the measuring method of the drug using the preprocessing column for measuring the drug of the present invention is specifically described as follows. That is, first, after adjusting the conditioning of the column by the known method, (1) The sample containing the drug is passed through the preprocessing column for measuring the drug of the present invention to adsorb the drug onto the column (filler). Method of passing the liquid may be free fall, or may be carried out by pressurization or depressurization, and pressurization or depressurization method is preferable. When pressurization or depressurization method is employed, adsorption rate is decreased when flow rates of the sample become too high. Therefore, flow rates of the sample are determined normally at 1 to 30 mL/min, preferably at 10 to 30 mL/min, more preferably at 10 to 20 mL/min. It should be noted that, when pH of the sample having the acidic drug is 8 or more, it is preferable to pass the liquid after adjusting pH of the sample to 7 or less by the known neutralization reaction. That is, it is considered that the acidic drugs are held by ion exchange capacity of the anion exchanging group in the polymer of the present invention, and therefore, in order to prevent the reduction of adsorption rate, pH of the sample is preferably adjusted to 7 or less. When washing is carried out after operation of (1), washing solution may be passed through column. As the washing solution, buffer solution having of pH 6 to 8 is used, and said buffer solution may be the one having 5 to 10% of aqueous organic solvent such as methanol, ethanol, propanol, acetonitrile, acetone, dichloromethane. The liquid amount of washing solution may be appropriately determined according to the amount of the filler, and it is normally 0.5 to 10 mL, preferably 0.5 to 5 mL relative to 10 mg of filler. It should be noted that, pH adjustment of washing solution may be carried out according to the method normally used in this field. Method of passing the liquid may be free fall, or may be carried out by pressurization or depressurization, and passing the liquid by pressurization or depressurization is preferable because the washing solution can be removed perfectly.

Next, (2) when the dugs adsorbed onto column are eluted by eluate, the neutral and basic drugs are eluted by the aqueous organic solvent such as methanol, ethanol, propanol, acetonitrile, acetone, dichloromethane, and acidic drug is eluted by the acidic aqueous solution or the acidified aqueous organic solvent such as methanol, ethanol, propanol, acetonitrile, acetone, dichloromethane having normally pH 1 to 3, preferably pH 1 to 2, and the like. pH adjustment of said acidic aqueous solution or acidic aqueous organic solvent is not particularly limited, as long as it is carried out by the method using the acidic compound normally used in this field. Said acidic compounds include, preferably, for example, hydrochloric acid, nitric acid, acetic acid, formic acid and the like. A specific adjusting method is carried out as follows. For example, when pH is adjusted to 1 to 2 by using formic acid, the acidic aqueous solution or the acidic aqueous organic solvent may be adjusted so that formic acid may contain normally 1 to 5 w/w %, preferably 1 to 2 w/w % as a concentration in the eluate. Amount of the eluate in the elution of the above-described (2) may be appropriately determined according to the amount of filler, and it is normally 0.3 to 100 mL, preferably 0.3 to 10 mL, more preferably 0.3 to 1 mL relative to 10 mg of the filler.

Further, (3) by measuring the eluate containing the eluted drugs with the known separation measurement method, amount or concentration of the drug in the sample can be obtained. If necessary, after the eluate containing the drug, which is used in separation measurement, is condensed by the known method, the elute may be provided with the separation measurement method. The separation measurement methods include, for example, liquid chromatography method, gas chromatography method, electrophoretic method and the like, and as detection tool, UV detection, fluorescence detection, MS, MS/MS, evaporative light scattering detection (ELSD) and the like known in itself may be used, and measurement condition and the like may be determined according to the one which is normally employed in this field.

More specifically, for example, the measurement method is carried out as follows. That is, for example, when 10 mL of the sample having 1 to 10 μg/mL of drugs is used, the column filled with 50 to 100 mg of the filler for measuring the drug of the present invention is used. 2 to 5 mL of aqueous organic solvent such as methanol, 2 to 5 ml of purified water, and 2 to 5 mL of buffer solution of sodium acetate having pH 6 to 8 are sequentially passed through said column, and thus, column condition is adjusted. Next, 10 mL of the sample is passed through the column. Then, it is washed by passing 1 to 3 mL of the buffer solution of 0.1 to 1 mol/L of sodium acetate having 5 to 10% of methanol. Next, 2 to 5 mL of methanol is passed to elute the neutral and basic target drug. Further, 2 to 5 mL of methanol having pH 1 to 2 is passed through to elute the acidic target drugs. Each of the obtained eluates is separated with HPLC at the setting condition which is normally carried out in this field, and the target drugs are measured by UV, fluorescent detector and the like, and therefore, the amount of the target drug in the sample is obtained. It should be noted that, the acidic drugs, and the neutral and basic target drugs may be eluted into one container, and the acidic, neutral and basic drugs may be simultaneously analyzed by separation.

Next, the present invention is described in more detail by the Examples. However the present invention is not limited by these Examples.

Example 1

Synthesis of Polymer-1 of the Present Invention

As a hydrophobic monomer, 85.0 g of divinylbenzene (produced by Nippon Steel Chemical Co., Ltd.) (purity: 80%) (containing 0.52 mol of pure divinylbenzene), as a polar monomer (monomer in which ion exchanging group can be introduced), 15.0 g (0.106 mol) of glycidyl methacrylate (produced by Wako Pure Chemical Industries, Ltd) were used, and as a water-insoluble organic solvent, 100 g of toluene was used. 1.0 g of azobisisobutyronitrile (produced by Wako Pure Chemical Industries, Ltd.) was added to mixed solvent of 2 kinds of the above-described monomers and the water-insoluble organic solvent, and dissolved. Then, mixed solution was suspended in 0.8 Lgggg of 0.2% by weight aqueous solution of methylcellulose, and was stirred at high speed to adjust the average diameter of oil droplet to about 60 μm. Then, mixed solution was transferred to polymerization apparatus equipped with stirrer, and was reacted at 80° C. for 6 hours to obtain the cross-linked porous copolymerized particles. These particles were washed with 2 L of water and 2 L of methanol after filtering, and were dipped in ethyl acetate overnight. Then, these particles were washed with 2 L of methanol and dried. The resultant cross-linked porous copolymerized particles had 10.26 nm of average micropore diameter and 636 $m^2/g$ of specific surface area. These particles were classified with 32 μm and 63 μm sieves.

10.0 g of porous copolymer after classification was dispersed in 50 mL of 50% aqueous solution of 2-propanol to provide homogeneous slurry, and was transferred to the reaction apparatus equipped with stirrer, and amination reaction was carried out by adding 18.5 g (0.21 mol) of morph line (produced by Wako Pure Chemical Industries, Ltd) at 50° C. for 20 hours. After reaction completed, reaction product was sequentially washed with water and methanol, and was dried, thus, the resultant polymer was defined as polymer-1 of the present invention. It should be noted that, content of morpholino group in the resultant polymer-1 of the present invention was 0.45 mmol/g. In addition, structure of polymer-1 of the present invention is shown as follows.

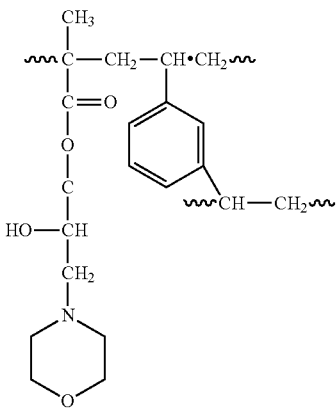

Example 2

Synthesis of Polymer-2 of the Present Invention

Cross-linked porous copolymerized particles were obtained using the similar procedure to Example 1. The obtained cross-linked porous copolymerized particles had 10.56 nm of average micropore diameter and 662.5 $m^2/g$ of specific surface area. These particles were classified using 32 μm and 63 μm sieves. Diethylamino group was introduced to the porous copolymer by the similar procedure to Example 1 except that 15.5 g of diethylamine (produced by Wako Pure Chemical Industries, Ltd) was used instead of 18.5 g of morph line, and thus, the resultant polymer was defined as polymer-2 of the present invention. It should be noted that, content of diethylamino group in the obtained polymer-2 of the present invention was 0.56 mmol/g. In addition, structure of polymer-2 of the present invention is shown as follows.

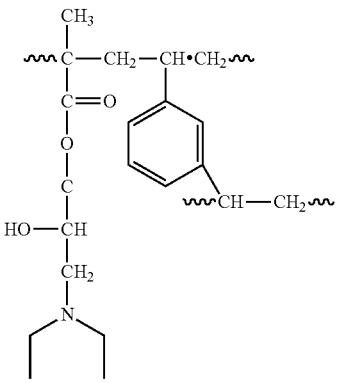

Example 3

Addition and Recovery Experiment of the Perfluoro Compound Having the Acidic Group (PFCs) Using Polymer-1 of the Present Invention, Polymer-2 of the Present Invention 1. Preparation of Column and Sample 1-1. Preparation of Column Each of 60 mg of Polymer-1 and 60 mg of polymer-2 of the present invention prepared in Example 1 and Example 2 was filled into the 3 ml of polypropylene syringes (manufactured by Pronics Co. Ltd) equipped with filter having 20 μm of micropore diameter (Yoko Co., Ltd) at upper and lower ends respectively. These were defined as solid-phase extraction column-1 and solid-phase extraction column-2.

1-2. Preparation of the Sample

In 1000 ml of the purified water, 13 kinds of the perfluoro compounds having the acidic group [perfluoro sulfonic acids: PFBS (produced by Wako Pure Chemical Industries, Ltd); PFHx (produced by Wellington Co., Ltd); PFOS (produced by Accustandard, Inc.); PFDS (produced by Wellington Co., Ltd); perfluoro carboxylic acid: PFPeA, PFHxA, PFHpA, PFOA, PFNA, PFDA, PFUnDA (produced by Wako Pure Chemical Industries, Ltd), PFDoDA (produced by Hydrus Chemical Inc), PFTeDA (produced by Fluorochem Ltd)] were added by 20 ng respectively, and each was defined as sample-water.

As the above-described purified water, the purified water which was passed through the Presep-C PFC (Short: produced by Wako Pure Chemical Industries, Ltd) subjected to conditioning was used. It should be noted that, the purified water in the Examples of this application was the one treated by the same procedure.

In addition, each of 13 kinds of the perfluoro compounds having the acidic group (perfluorosulfonic acids: PFBS, PFHxS, PFOS, PFDS; perfluoro carboxylic acids: PFPeA, PFHxA, PFHpA, PFOA, PFNA, PFDA, PFUnDA, PFDoDA, PFTeDA) was dissolved in methanol to prepare the solution having by 20 ng/2 mL respectively. Each of methanolic solutions containing the obtained 13 kinds of the perfluoro compound having the acidic group respectively was defined as standard sample.

2. Solid-Phase Extraction by Column
  (1) Conditioning of the Column
  Conditioning was carried out by passing 5 ml of methanolic solution having 0.1% of ammonia, 5 mL of methanol (methanol for LC/MS: produced by Wako Pure Chemical Industries, Ltd), and 10 ml of purified water sequentially by free fall respectively into solid-phase extraction column-1 and solid-phase extraction column-2.
  (2) Passing the Sample Solution
  1000 mL of the sample water was passed through by using aspiration manifold (manufactured by JT Baker Inc) in which depressurization force was set so as to obtain 10 to 20 mL/min of flow rates.
  (3) Washing
  By using aspiration manifold (manufactured by JT Baker Inc) in which depressurization force was set so as to obtain 1 to 2 mL/min of flow rates, solid-phase extraction column was washed with 5 mL of purified water, and further, water was removed from the column while aspirating for 5 minutes.
  (4) Elution
  Two mL of the methanolic solution having 0.1% ammonia was passed by 2 times free fall and eluted, and each of eluates obtained by 2 times elution was taken into 2 mL of graduated disposable spits (manufactured by Falcon Co. Ltd) made of polypropylene (made of PP) respectively.
  (5) Preparation of the Test Solution
  To each of the obtained eluates, methanol (methanol for LC/MS: produced by Wako Pure Chemical Industries, Ltd) was added to adjust to 2 mL of volume, and this solution was defined as the test solution. In addition, all the used apparatuses were reused after washing with methanol and drying in order to remove contamination of PFCs
3. Measurement Results by LC/MS/MS Method
  Two test solutions (first eluate and second eluate) obtained from the above-described operation of solid-phase extraction and the standard samples were analyzed by LC/MS/MS. Area value obtained from analysis of the standard samples was specified as 100%, and recovery rate of the test solutions was determined. These results were shown in Table-1. In addition, measurement condition of LC/MS/MS was shown as follows:
  [HPLC Condition]
    Column: Wakopak Navi C18-5, 2.0×150 mm (manufactured by Wako Pure Chemical Industries, Ltd);
    Eluate: A) 10 mM ammonium acetate aqueous solution; B) acetonitrile;
    Time program: 0-25 min B=35-90%, 25-30 min B=90%, 30-35 min B=90-35%, 35-40 min B=35%;
    flow rates: 0.2 mL/min, column temperature: 40° C.;
    amount of injection: 5 μL;
  [LC/MS/MS: Ionization Condition]
    Curtain Gas (CUR): 10;
    Collision Gas (CAD): 5;
    Ion Spray Voltage (IS): −4500;
    Temperature (TEM): 400;
    Ion Source Gas1 (Gas1): 80;
    Ion Source Gas2 (Gas2): 70;
  Each detective ion of the perfluoro compounds having the acidic group (Q1 and Q3) is shown as follows:

TABLE 1

| | Compound | LC/MS/MS Detected Ion (atomic mass unite) | Recovery rate (%) by solid-phase extraction column-1 | | | Recovery rate (%) by solid-phase extraction column-2 | | |
|---|---|---|---|---|---|---|---|---|
| | | | First elution | Second elution | Sum | First elution | Second elution | Sum |
| 1 | PFBS | 298.8/79.6 amu | 96 | 2.2 | 99 | 95 | 0.8 | 96 |
| 2 | PFHxS | 398.8/79.6 amu | 92 | 1.1 | 93 | 106 | 0.3 | 106 |
| 3 | PFOS | 498.8/79.6 amu | 99 | 1.7 | 101 | 98 | 1.4 | 100 |
| 4 | PFDS | 598.9/79.9 amu | 91 | 0.2 | 91 | 90 | 0.0 | 90 |
| 5 | PFPeA | 262.8/219.1 amu | 102 | 1.6 | 104 | 98 | 0.8 | 99 |
| 6 | PFHxA | 312.9/268.6 amu | 93 | 3.5 | 97 | 86 | 1.3 | 87 |
| 7 | PFHpA | 362.8/318.7 amu | 98 | 3.3 | 101 | 97 | 2.6 | 99 |
| 8 | PFOA | 412.9/368.9 amu | 102 | 5.8 | 108 | 100 | 4.3 | 104 |
| 9 | PFNA | 462.7/418.8 amu | 102 | 0.8 | 102 | 102 | 0.0 | 102 |
| 10 | PFDA | 512.9/469.0 amu | 99 | 0.9 | 100 | 83 | 0.0 | 83 |
| 11 | PFUnDA | 562.9/519.0 amu | — | — | — | 86 | 1.1 | 87 |
| 12 | PFDoDA | 612.9/568.9 amu | — | — | — | 81 | 0.2 | 81 |
| 13 | PFTeDA | 712.9/669 amu | — | — | — | 96 | 0.5 | 96 |

As apparent from the above-described Table-1, as a result of solid phase extraction using column-1 and 2 of the present invention, it was found that various perfluoro compounds having the acidic group can be extracted with 80% or more of high recovery rate by using any columns. Further, in the column-1 of the present invention, all of the 10 kinds of the perfluoro compounds having the acidic group have shown 90% or more of recovery rate. Also, in the column-2 of the present invention, the perfluoro sulfonic acids have shown 90% or more of recovery rate. That is, even in any columns, significantly high recovery rate was found to show in the perfluoro compound having the acidic group having 10 or less of carbon atoms. As for elution, it was found that target substances were almost completely eluted by 2 mL of the first eluate in case of 60 mg of the filler of the present invention because elution effect by second elution (2 mL) was weak.

Example 4

Addition and Recovery Experiment of the Perfluoro Compound Having the Acidic Group (PFCs) Using Polymer-1 of the Present Invention 1. Preparation of Column and Sample
1-1. Preparation of Column
Into the 3 ml of polypropylene syringe (manufactured by Pronics Co. Ltd) equipped with filter having 20 μm of micropore diameter (Yoko Co., Ltd), 60 mg of Polymer-1 of the present invention prepared in Example 1 was filled. This was defined as solid-phase extraction column-3
2. Solid-Phase Extraction by Column
Solid-phase extraction was carried out by the similar way to Example 3 except that elution was one time.
3. Measurement Results by LC/MS/MS Method
The liquid obtained by the solid-phase extraction operation and the standard samples were analyzed relatively by LC/MS/MS. Area value obtained from analysis of the standard samples was specified as 100%, and recovery rate of the test solution was determined. These results were shown in Table-2. In addition, measurement condition of LC/MS/MS was the same as Example 3.

TABLE 2

|   | Perfluoro compound | Recovery rate (%) by solid-phase extraction column-3 |
|---|---|---|
| 1 | PFBS | 100 |
| 2 | PFHxS | 90 |
| 3 | PFOS | 92 |
| 4 | PFDS | 90 |
| 5 | PFPeA | 86 |
| 6 | PFHxA | 90 |
| 7 | PFHpA | 90 |
| 8 | PFOA | 92 |
| 9 | PFNA | 100 |
| 10 | PFDA | 92 |
| 11 | PFUnDA | 94 |
| 12 | PFDoDA | 92 |
| 13 | PFTeDa | 92 |

From the result of Table-2, it was found that only the recovery rate of PFPeA (perfluoro pentanoic acid) was 86%, and all of the other recovery rates were more than 90%, and all of the perfluoro compounds having the acidic group can be recovered by 80% or more when the polymer-1 of the present invention was employed. Therefore, most of the compounds have shown 90% or more of recovery rate.

Comparative Example 1

Addition and Recovery Experiment of PFCs Using Presep-C Agri (Short) Column

1. Preparation of Column and Sample
1-1. Column
Commercially available Presep-C Agri (Short) (220 mg, closed type column, manufactured by Wako Pure Chemical Industries, Ltd) was used. It should be noted that, structure of Presep-C Agri was shown as follows:

$$\begin{array}{c} CH_3 \\ | \\ \sim\!\!\sim\!\!\sim C - CH_2 - CH \cdot CH_2 \sim\!\!\sim\!\!\sim \\ | \\ C=O \\ | \\ O \\ | \\ CH_2 \\ | \\ CH_2 \\ | \\ O \\ | \\ C=O \\ | \\ \sim\!\!\sim\!\!\sim C - CH_2 \sim\!\!\sim\!\!\sim \\ | \\ CH_3 \end{array} \quad \begin{array}{c} \\ \\ \\ \\ \\ \sim\!\!\sim\!\!\sim CH - CH_2 \sim\!\!\sim\!\!\sim \end{array}$$

1-2. Preparation of Sample
To 1000 ml of the purified water, 13 kinds of the perfluoro compounds having the acidic group (perfluoro sulfonic acid: PFBS, PFHx, PFOS, PFDS, perfluoro carboxylic acid having the acidic group: PFPeA, PFHxA, PFHpA, PFOA, PFNA, PFDA, PFUnDA, PFDoDA, PFTeDA) were added by 20 ng respectively. This solution was defined as sample water. Also, each of 13 kinds of the perfluoro compounds having the acidic group (perfluorosulfonic acid: PFBS, PFHx, PFOS, PFDS, perfluorocarboxylic acid: PFPeA, PFHxA, PFHpA, PFOA, PFNA, PFDA, PFUnDA, PFDoDA, PFTeDA) was dissolved in methanol to adjust the solution to 20 ng/2 mL respectively. Each solution was defined as the standard sample.
2. Solid-Phase Extraction by Column
(1) Conditioning of Column
10 mL of methanol (methanol for LC/MS, produced by Wako Pure Chemical Industries, Ltd) and 10 mL of purified water were passed sequentially through Presep-C Agri by free fall.
(2) Passing of the Sample Solution
1000 mL of the sample water was passed through by using aspiration manifold (manufactured by JT Baker Inc) in which depressurization force was set so as to obtain 10 to 20 mL/min of flow rates.
(3) Washing
By using aspiration manifold (manufactured by JT Baker Inc) in which depressurization force was set so as to obtain 1 to 2 mL/min of flow rates, column was washed with 5 mL of purified water, and further, aspirating was continued for 5 minutes to remove water from the column.
(4) Elution
2 mL of methanol (methanol for LC/MS: produced by Wako
Pure Chemical Industries, Ltd) was passed by free fall 2 times and eluted, and each of eluates obtained by 2 times elution was taken into 2 mL of graduated disposable spits made of PP respectively.
(5) Preparation of the Test Solution
To each of the obtained eluates, methanol (methanol for LC/MS: produced by Wako Pure Chemical Industries, Ltd) was added to adjust 2 mL of volume respectively, and this solution was defined as the test solution. In addition, all the used apparatuses were reused after washing with methanol and drying in order to remove contamination of PFCs
3. Measurement Results by LC/MS/MS Method
Two test solutions obtained from the above-described operation of solid-phase extraction (first eluate and second eluate) and standard samples were analyzed by LC/MS/MS. Area value obtained from analysis of standard samples was specified as 100%, and recovery rate of the test solutions were determined. These results were shown in Table-3. In addition, measurement condition of LC/MS/MS was the same as Example-3.

TABLE 3

| | Perfluoro Compounds | Recovery rate by Presep-C Agri (Short) (%) | | |
|---|---|---|---|---|
| | | First Elution | Second Elution | Sum |
| 1 | PFBS | 16 | 0.1 | 16 |
| 2 | PFHxS | 82 | 1.9 | 84 |
| 3 | PFOS | 93 | 0.2 | 93 |
| 4 | PFDS | 93 | 1.0 | 94 |
| 5 | PFPeA | 9 | 0.2 | 10 |
| 6 | PFHxA | 18 | 0.7 | 19 |
| 7 | PFHpA | 47 | 0.8 | 48 |
| 8 | PFOA | 92 | 1.4 | 93 |
| 9 | PFNA | 98 | 1.0 | 99 |
| 10 | PFDA | 93 | 1.1 | 94 |
| 11 | PFUnDA | 91 | 1.2 | 92 |
| 12 | PFDoDA | 85 | 1.4 | 87 |
| 13 | PFTeDa | 74 | 2.0 | 76 |

As apparent from results of the above-described Table-3, in case of use of Presep-C Agri column containing the hydrophilic reversed-phase polymer resin, each of recovery rates for perfluoro sulfonic acids having 4 or less of carbon atoms, and perfluoro carboxylic acids having 7 or less of carbon atoms was 50% or less. In addition, recovery rate of PFTeDA having 14 carbon atoms was less than 80%. Therefore, it was shown that Presep-C Agri column can be used to solid-phase extraction of specified perfluoro compounds having the acidic group, but it was unsuitable for measuring simultaneously all the perfluoro compounds having the acidic group.

Comparative Example 2

Addition and Recovery Experiment of the Perfluoro Compound Having the Acidic Group (PFCs) Using Oasis HLB 1. Preparation of Column and Sample
1-1. Column
Commercially available Oasis HLB (225 mg, closed type: manufactured by Waters Corp) was used.
1-2. Preparation of Sample
To 1000 ml of the purified water, 13 kinds of the perfluoro compounds having the acidic group (perfluoro sulfonic acid: PFBS, PFHx, PFOS, PFDS, perfluoro carboxylic acid: PFPeA, PFHxA, PFHpA, PFOA, PFNA, PFDA, PFUnDA, PFDoDA, PFTeDA) were added by 20 ng respectively. This solution was defined as sample water.
In addition, each of 13 kinds of the perfluoro compounds having the acidic group (perfluorosulfonic acid: PFBS, PFHx, PFOS, PFDS, perfluorocarboxylic acid: PFPeA, PFHxA, PFHpA, PFOA, PFNA, PFDA, PFUnDA, PFDoDA, PFTeDA) was dissolved in methanol to adjust the solution to 20 ng/4 mL respectively. Each solution was defined as the standard sample.
2. Solid-Phase Extraction by Column
(1) Conditioning of Column
5 ml of methanol (methanol for LC/MS: produced by Wako Pure Chemical Industries, Ltd) and 5 ml of purified water were passed sequentially by free fall into Oasis HLB. It should be noted that, structure of filler of Oasis HLB was shown as follows.

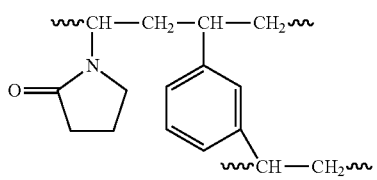

(2) Passing the Sample Solution
1000 mL of the sample water was passed through by using aspiration manifold (manufactured by JT Baker Inc) in which depressurization force was set so as to obtain 10 to 20 mL/min of flow rates.
(3) Washing
By using aspiration manifold (manufactured by JT Baker Inc) in which depressurization force was set so as to obtain 1 to 2 mL/min of flow rates, column was washed with 5 mL of purified water, and further, water was removed from the column while further aspirating for 5 minutes.
(4) Elution
Four mL of methanol was passed by free fall and was eluted, and eluate was taken into 4 mL of graduated disposable spits made of PP.
(5)
To the obtained eluate, methanol (methanol for LC/MS: produced by Wako Pure Chemical Industries, Ltd) was added to adjust 4 mL of volume. This solution was defined as test solution. In addition, all the used apparatuses were reused after washing with methanol and drying in order to remove contamination of PFCs
3. Measurement Results by LC/MS/MS Method
The test solution obtained by the above-described operation of solid-phase extraction and the standard samples were analyzed by LC/MS/MS respectively. Area value obtained from analysis of the standard sample was specified as 100%, and recovery rates of the test solution were determined. These results were shown in Table-4. In addition, measurement condition of LC/MS/MS was the same as Example 3.

Comparative Example 3

Addition and Recovery Experiment of the Perfluoro Compound Having the Acidic Group (PFCs) Using Oasis WAX 1. Preparation of Column and Sample
1-1. Column
Commercially available Oasis WAX (225 mg, closed type, manufactured by Waters Corp) was used.
1-2 Preparation of the Sample
To 1000 ml of the purified water, 13 kinds of the perfluoro compounds having the acidic group (perfluoro sulfonic acid: PFBS, PFHx, PFOS, PFDS, perfluoro carboxylic acid: PFPeA, PFHxA, PFHpA, PFOA, PFNA, PFDA, PFUnDA, PFDoDA, PFTeDA) were added by 20 ng respectively. Each solution was defined as sample water. In addition, each of 13 kinds of the perfluoro compounds having the acidic group (perfluorosulfonic acid: PFBS, PFHx, PFOS, PFDS, perfluorocarboxylic acid: PFPeA, PFHxA, PFHpA, PFOA, PFNA, PFDA, PFUnDA, PFDoDA, PFTeDA) was dissolved in methanol to adjust the solution to 20 ng/4 mL respectively. Each solution was defined as standard sample.
2. Solid-Phase Extraction by Column
(1) Conditioning of Column
Five ml of methanol (methanol for LC/MS: produced by Wako Pure Chemical Industries, Ltd) and 5 ml of purified water were passed sequentially by free fall into Oasis WAX. It should be noted that, structure of filler of Oasis WAX was shown as follows.

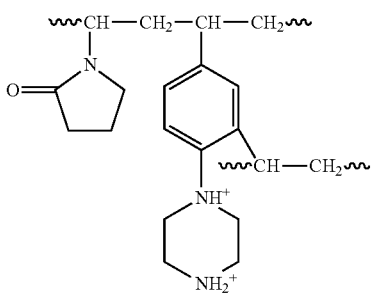

(2) Passing the Sample Solution

By using aspiration manifold (manufactured by JT Baker Inc) in which depressurization force was set so as to obtain 10 to 20 mL/min of flow rates, 1000 mL of the sample water was passed through.

(3) Washing

By using aspiration manifold (manufactured by JT Baker Inc) in which depressurization force was set so as to obtain 1 to 2 mL/min of flow rates, column was washed with 2 mL of methanol, and further aspirating was continued for 5 minutes to remove water from column.

(4) Elution

Four ml of methanol having 1% of ammonia was passed through by free fall and eluted, and eluate was taken into 4 mL of graduated disposable spits (manufactured by Falcon Co. Ltd) made of PP.

(5) Preparation of the Test Solution

To the obtained eluates, methanol (methanol for LC/MS: produced by Wako Pure Chemical Industries, Ltd) was added to adjust to 4 mL of volume, and this solution was defined as the test solution. It should be noted that, all the used apparatuses were used after washing with methanol and drying in order to remove contamination of PFCs 3. Measurement Results by LC/MS/MS Method The test solution obtained by the above-described operation of solid-phase extraction and standard samples were analyzed by LC/MS/MS respectively. Area value obtained from analysis of the standard sample was specified as 100%, and recovery rate of the test solution was determined. These results were shown in Table-4 in addition. It should be noted that, measurement condition of LC/MS/MS was the same as Example 3.

TABLE 4

|  | Perfluoro compound | Recovery rate by Oasis HLB (%) | Recovery rate by Oasis WAX (%) |
|---|---|---|---|
| 1 | PFBS | 92 | 85 |
| 2 | PFHxS | 94 | 92 |
| 3 | PFOS | 92 | 101 |
| 4 | PFDS | 80 | 84 |
| 5 | PFPeA | 90 | 88 |
| 6 | PFHxA | 96 | 90 |
| 7 | PFHpA | 94 | 92 |
| 8 | PFOA | 96 | 94 |
| 9 | PFNA | 96 | 104 |

TABLE 4-continued

|  | Perfluoro compound | Recovery rate by Oasis HLB (%) | Recovery rate by Oasis WAX (%) |
|---|---|---|---|
| 10 | PFDA | 96 | 96 |
| 11 | PFUnDA | 92 | 90 |
| 12 | PFDoDA | 72 | 76 |
| 13 | PFTeDa | 50 | 64 |

As apparent from results of Table-4, in case of using Oasis HLB and Oasis WAX, recovery rates of PFDoDA (perfluorododecyl carboxylic acid) and PFTeDA (perfluorotetradecanoic acid) which have 12 and over carbon atoms were less than 80%, particularly PFTeDA having 14 carbon atoms (perfluorotetradecanoic acid) showed low recovery rate less than 70% in any case.

As described above, it was found that, from results of Table-3, Table-4, in case of using Presep-C Agri column in which hydrophilic reversed polymer resin was used for recovering the perfluoro compounds having the acidic group, recovery rate of the compound having small carbon numbers (7 or less) or large carbon numbers (14 or more) becomes low. In case of using commercially available Oasis HLB, Oasis WAX for recovering the perfluoro compounds having the acidic group, recovery rate of the compound having large carbon numbers (12 or more) becomes low. On the other hand, as apparent from results of Table-1, and Table-2, when the columns of the present invention were used, 80% or more of recovery rates were shown in all the perfluoro compounds having the acidic group regardless of carbon numbers. Depending on the kind of the introduced anion exchanging group, most of the perfluoro compounds having the acidic group can be recovered by 90% or more of high recovery rate. Therefore, it was found that the perfluoro compounds having acidic group at terminal such as perfluoro sulfonic acid, perfluoro carboxylic acid could be efficiently and simultaneously measured regardless of carbon numbers when the column of the present invention was used.

Example 5

Synthesis of Polymer-3 of the Present Invention

As a hydrophobic monomer, 85.0 g of divinylbenzene (produced by Nippon Steel Chemical Co., Ltd: purity: 57%) (contained 0.37 mol of pure divinylbenzene), as a polar monomer (monomer in which ion exchanging group can be introduced), 15.0 g of glycidyl methacrylate (containing 0.106 mol of glycidyl methacrylate) (produced by Wako Pure Chemical Industries, Ltd) were used, and 100 g of toluene was used as a water-insoluble organic solvent. After 1.0 g of azobisisobutyronitrile (produced by Wako Pure Chemical Industries, Ltd.) was added to this mixture and dissolved. Mixed solution was suspended in 0.8 L of aqueous solution having 0.2% by weight of methylcellulose, and was stirred at high speed to adjust the average diameter of oil droplet at about 60 μm. Then, mixed solution was transferred to polymerization apparatus equipped with stirrer and reacted at 80° C. for 6 hours to obtain the cross-linked porous copolymerized particles. These particles were filtered, and were further washed with 2 L of water and 2 L of methanol, and were dipped in ethyl acetate overnight. Then, these particles were washed with 2 L of methanol and dried. It should be noted that, the resultant cross-linked porous copolymerized particles had 4.0 nm of average micropore diameter and 429 m²/g of specific surface area. Said particles were classified with 32 μm and 63 μm sieves to obtain 37 g of particles having about 40 μm of average particle diameter.

After classification, 10.0 g of the obtained porous copolymer was dispersed in 50 mL of aqueous solution having 50% of 2-propanol to provide homogeneous slurry, and was transferred to the reaction apparatus equipped with stirrer, and amination reaction was carried out by adding 15 g (0.17 mol) of N,N-dimethylaminoethane (produced by Wako Pure Chemical Industries, Ltd) at 40° C. for 20 hours. After the reaction completed, reaction product was sequentially washed with water and methanol, and dried, and thus, polymer-3 of the present invention was obtained. Content of introduced ethyldimethyl ammonium group (anion exchanging group) was determined by reverse titration method, and then amount of this group was shown as 0.34 meq/g gel dry. It should be noted that, structure of polymer-3 of the present invention is shown as follows.

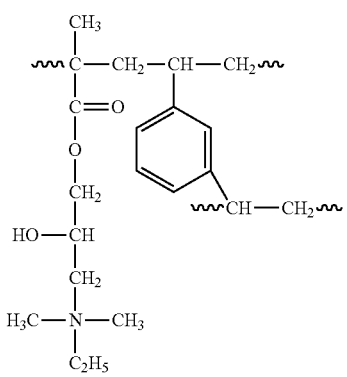

Example 6

Synthesis of Polymer-4 of the Present Invention

The cross-linked porous copolymeric particles were obtained by using the reagent and the procedure similar to Example 5 except that as a hydrophobic monomer, 80.0 g of divinylbenzene (produced by Nippon Steel Chemical Co., Ltd, purity: 57%) (contained 0.37 mol of pure divinylbenzene), as a polar monomer (monomer in which ion exchanging group can be introduced), 15.0 g of glycidyl methacrylate (contained 0.106 mol of glycidyl methacrylate) (produced by Wako Pure Chemical Industries, Ltd) and triallyl isocyanurate (produced by Tokyo Chemical Industry Co., Ltd) (contained 0.02 mol of triallyl isocyanurate) were used. The cross-linked porous copolymeric particles were washed by the similar way, then dried. These cross-linked porous copolymeric particles had 3.9 nm of average micropore diameter and 380 m²/g of specific surface area. After these particles were classified by using 32 μm and 63 μm sieves, ethyldimethylammonium group was introduced by the method similar to Example-5, and polymer-4 of the present invention was obtained. Content of the introduced ethyldimethylammonium group (anion exchanging group) was determined by reverse titration method, and amount of this group was 0.30 meq/g gel dry. It should be noted that, structure of polymer-4 of the present invention was shown as follows.

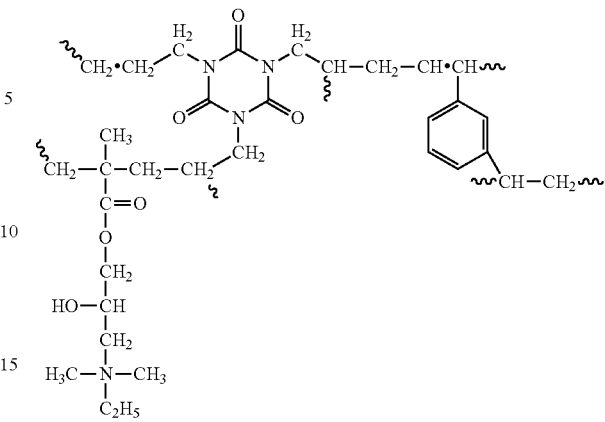

Comparative Example 4

Synthesis of Comparative Polymer-1

The cross-linked porous copolymeric particles were obtained by using the reagent and the procedure similar to Example 5 except that as a hydrophobic monomer, 65.0 g of divinylbenzene (produced by Nippon Steel Chemical Co., Ltd, purity: 57%) (contained 0.28 mol of pure divinylbenzene), as a polar monomer (monomer in which ion exchanging group can be introduced), 30.0 g of glycidyl methacrylate (produced by Wako Pure Chemical Industries, Ltd) (contained 0.21 mol of glycidyl methacrylate) and 5 g of dimethylacrylamide (produced by Wako Pure Chemical Industries, Ltd) (contained 0.05 mol of dimethylacrylamide), as a water-insoluble organic solvent, 60 g of toluene, and 40 g of lauryl alcohol were used. These resin particles were washed by the similar way, then dried. These cross-linked porous copolymerized particles had 29.8 nm of average micropore diameter and 260 m²/g of specific surface area. After classification of these particles with 32 μm and 63 μm sieves, trimethylamino group was introduced by using the reagent and the procedure similar to Example 5 except that reaction time is 6 hours, and 40 g of trimethylamine (produced by Wako Pure Chemical Industries, Ltd, 30% of aqueous solution) instead of N,N-dimethylethaneamine was used, and comparative polymer-1 was obtained. Amount of the introduced anion exchanging group was determined by reverse titration method, and it was 0.29 meq/g gel dry. It should be noted that, structure of comparative polymer-1 was shown as follows.

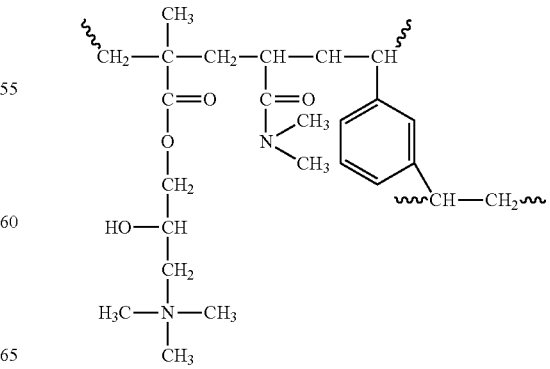

Comparative Example 5

Production of Comparative Polymer-2

As a hydrophobic monomer, 70.0 g of divinylbenzene (produced by Nippon Steel Chemical Co., Ltd, purity: 57%) (contained 0.306 mol of pure divinylbenzene), as a polar monomer (monomer in which ion exchanging group can be introduced), 20.0 g of chloromethylstyrene (produced by Tokyo Chemical Industry Co., Ltd, purity: 90%) (contained 0.146 mol of pure chloromethylstyrene), as a polar monomer, 10.0 g of dimethylacrylamide (produced by Wako Pure Chemical Industries, Ltd) (contained 0.1 mol of dimethylacrylamide) were used. As a water-insoluble organic solvent, 60 g of toluene, 40 g of lauryl alcohol were used. As polymerization initiator, 1.0 g of azobisisobutyronitrile (produced by Wako Pure Chemical Industries, Ltd) was dissolved in this mixture, and then, mixed solution was suspended in 0.8 L of aqueous solution having 0.2% by weight of methylcellulose, and stirred at high speed to adjust the average diameter of oil droplet to about 40 μm. Then, mixed solution was transferred to polymerization apparatus equipped with stirrer, and reacted at 80° C. for 6 hours to obtain the cross-linked porous copolymerized particles. These particles were filtered, and further washed with 2 L of water and 2 L of methanol, and dipped in ethyl acetate overnight. Subsequently, these particles were washed with 2 L of methanol, and dried. It should be noted that, the cross-linked porous copolymeric particles obtained by such method had 3.8 nm of average micropore diameter and 96 m$^2$/g of specific surface area. Said particles were classified by using 32 μm and 63 μm of sieves, and 35 g of particles having about 40 μm of average particle diameter were obtained.

10.0 g of the obtained porous copolymer after classification was dispersed in 50 mL of aqueous solution having 50% of 2-propanol to provide homogeneous slurry, and transferred to the reaction apparatus equipped with stirrer, and amination reaction was carried out by adding g of N,N-dimethylaminoethane (produced by Wako Pure Chemical Industries, Ltd) at 40° C. for 8 hours. After the reaction completed, reaction product was sequentially washed with water and methanol, and dried, and thus, comparative polymer-2 was obtained. Amount of the introduced anion exchanging group was determined by reverse titration method, and it was 0.34 meq/g gel dry. It should be noted that, structure of comparative polymer-2 was shown as follows.

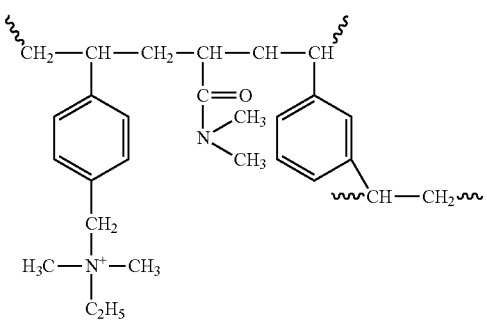

Example 7

Addition and Recovery Experiment of the Various Drug

To 6 mL of buffer solution of 2 mol/L of sodium acetate adjusted at pH 7, all the 8 kinds of drugs shown as Table-5 were added to prepare the test solutions containing the amount of drugs shown in the table. It should be noted that, as for the drug poorly soluble in the buffer solution of sodium acetate, once the drug of amounts in the table were dissolved in methanol, then said methanol was added to buffer solution.

In addition, into 2 mL of methanol, the amounts of 8 kinds of the drugs described in the right column of in Table-1 were added, and thus, the standard solution was prepared.

TABLE 5

| Drug | Amount of Drug in Test solution (μg) | Amount of Drug in Standard Solution (μg) |
|---|---|---|
| Theophylline | 5 | 5 |
| Scopolamine hydrobromide | 25 | 25 |
| caffeine | 5 | 5 |
| Atropine sulfate | 25 | 25 |
| Barbital | 10 | 10 |
| Nortriptylin | 10 | 10 |
| Salicylic acid | 20 | 10 |
| Naproxen | 20 | 10 |

As fillers, polymer-3, 4 of the present invention, comparative polymer-1, 2, and Oasis MAX were used, and these fillers were filled into the syringe type cartridges having 4 mL of inner volume by 60 mg respectively. These cartridges were defined as solid-phase extraction cartridges.

Addition and recovery experiments were carried out as follows. That is, first, to the solid-phase extraction cartridge, 2 mL of methanol, 2 mL of purified water and 1 mL of buffer solution having 2 mol/L of sodium acetate adjusted to pH 7 were passed, and then, total volume of the above-described test solution was poured. Subsequently, 2 mL of mixed solution of 95 mL of buffer solution having 0.1 mol/1 L of sodium acetate adjusted to pH 7 and 5 mL of methanol were passed to the same cartridge to wash. Then, 2 mL of methanol was passed through solid-phase extraction cartridge to elute the adsorbed materials adsorbed on solid-phase. 2 mL of recovered solution was separated with HPLC, and by measuring UV absorption thereof, and recovery rates were determined. The obtained recovery rates (%) are shown in Table-2. It should be noted that, value of UV absorption for which the standard solution was directly separated and measured by HPLC at the same condition was specified as standard value (100%), and the recovery rate was calculated from the standard value (hereinafter, same). In addition, HPLC condition was as follows.

[HPLC Condition]

Column: Wakopak Wakosil-II 5C18 HG, 4.6×150 mm;

Eluate: A) 0.1% of phosphoric acid B) acetonitrile;

Gradient: 0-15 min, B: 5-85%, 15-25 min: B: 5%;

Flow rates: 1.0 mL/min at 40° C.;

Amount of injection: 5 μl;

Apparatus: HPLC: Prominence system (Shimadzu);

Further, in order to elute the acidic compounds, 4 mL of methanolic solution containing 2% of formic acid was passed through. 4 mL of recovery solution eluted from the solid-phase cartridge was separated by HPLC at the above-described condition, and UV value thereof was measured, and then, recovery rates were determined. The obtained recovery rates (%) are shown in Table-3.

TABLE 6

| | | Addition Amount (μg/Column) | Filler | | | | |
|---|---|---|---|---|---|---|---|
| | Drug | | Polymer-3 | Polymer-4 | Comp. Polymer-1 | Comp. Polymer-2 | Oasis MAX |
| | | | Recovery rate (%) | | | | |
| Neutral Compound | Theophylline | 5 | 97.1 | 92.2 | 13.3 | 29.4 | 75.5 |
| | caffeine | 5 | 101.7 | 98.5 | 22.6 | 97.4 | 92.7 |
| | Barbital | 10 | 102.7 | 99.1 | 38.0 | 86.4 | 93.5 |
| Basic compound | Scopolamine hydrobromide | 25 | 106.6 | 103.0 | 50.7 | 58.7 | 94.0 |
| | Atropine sulfate | 25 | 108.0 | 105.7 | 11.9 | 96.6 | 67.5 |
| | Nortriptylin hydrochloride | 10 | 103.5 | 100.5 | — | 101.0 | 87.0 |
| Acidic Compound | Salicylic acid | 20 | 0 | 0 | — | 0 | 0 |
| | Naproxen | 20 | 0 | 0 | — | 0 | 0 |

TABLE 7

| | | Addition Amount (μg/Column) | Filler | | | | |
|---|---|---|---|---|---|---|---|
| | Drug | | Polymer-3 | Polymer-4 | Comp. Polymer-1 | Comp. Polymer-2 | Oasis MAX |
| | | | Recovery rate (%) | | | | |
| Acidic Compound | Salicylic acid | 20 | 106.8 | 104.6 | — | 67.5 | 103.4 |
| | Naproxen | 20 | 83.9 | 86.9 | — | 67.0 | 86.3 |

From the result of Table-6, it was found that by using polymer-3 and polymer-4 of the present invention, even Theophylline, Atropine sulfate, Nortriptylin hydrochloride and the like which have shown low recovery rate when Oasis MAX was used, can be recovered by almost 100% of recovery rate.

On the other hand, comparative polymer-1 having similar structure in part to polymer-3 and 4 of the present invention has shown as low recovery rate in any of neutral compound, basic compound. Similarly, comparative polymer-2 having similar structure in part to polymer-3 and 4 of the present invention has been shown as low recovery rate in Theophylline, Scopolamine hydrobromide. It is estimated that retention capability of neutral and basic compounds is greatly affected depending on the structure of polymer. Therefore, it was understood that the polymer structure comprising divinylbenzene and glycidyl methacrylate and the polymer structure comprising divinylbenzene, triallyl isocyanurate and glycidyl methacrylate, like polymer-3 and polymer-4 of the present invention, have contributed to high retention capability of neutral and basic compound.

Though salicylic acid and Naproxen of acidic compound were not eluted with methanol, as apparent from results of Table-7, these compounds can be eluted by methanol containing 2% of formic acid. According to these results, it was found that polymer-3 and 4 of the present invention have almost same recovery rate as Oasis MAX. Comparative polymer-2 has less than 70% of recovery rate in both salicylic acid and Naproxen, and it showed low value. Though retention capability of acidic compound was estimated to depend mainly on the anion exchanging group, according to this result, it was found that even when the same ion exchanging group (ethyldimethylammonium group) has been contained, retention capability of acidic compound may vary depending on the different structure of fundamental polymer structure. Therefore, it was found that by introducing the anion exchanging group to the polymer like polymer-3 and polymer-4 of the present invention, these polymers have excellent retention capability for neutral and basic compounds, as well as acidic compounds.

[Industrial Applicability]

The present invention relates to provide the novel polymer, and the filler comprising said polymer, and said filler can efficiently adsorb the various perfluoro compounds having the acidic group. Therefore, according to the solid-phase extraction method using said fillers, various perfluoro compounds having the acidic group can be simultaneously and efficiently measured. In addition, fillers comprising the above-described polymer can efficiently adsorb the drugs, and by solid-phase extraction method using said fillers, acidic, basic or/and neutral compounds can be efficiently measured.

The invention claimed is:

1. A method of measuring a perfluoro compound having an acidic group at a terminal, comprising steps of:
   contacting the perfluoro compound with a polymer,
      wherein the polymer includes a prepolymer having an anion exchange group attached to a gycidyl group of the prepolymer,
      the prepolymer is a polymerization product of a compound of formula [1]:

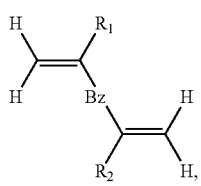

[1]

wherein each of $R_1$ and $R_2$ independently represents a hydrogen atom, a linear alkyl group having from 1 to 3 carbon atoms or a halogen atom, and Bz represents benzene ring, and a compound of formula [2]:

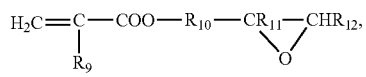

[2]

wherein $R_9$ represents a hydrogen atom, a linear alkyl group having from 1 to 3 carbon atoms or a halogen atom, $R_{10}$ represents a linear alkylene group having from 1 to 3 carbon atoms, and each of $R_{11}$ and $R_{12}$ independently represents a hydrogen atom or a linear alkyl group having from 1 to 6 carbon atoms, and a molar ratio of the compound of the formula [1]/ the compound of the formula [2] is in a range from 60/40 to 90/10; and measuring the perfluoro compound.

2. The method of claim 1, further comprising eluting at least a portion of the perfluoro compound with an eluting solution having a pH in arrange from 8 to 14.

3. The method of claim 2, further comprising subjecting an eluted portion of the perfluoro compound to mass spectrometry.

4. The method of claim 2, further comprising, prior to the eluting step, contacting at least a portion the perfluoro compound with a washing solution having a pH of 8 or less.

5. The method of claim 1, wherein the prepolymer is formed by mixing the compound of the formula [1] with the compound of the formula [2] in a non-aqueous, organic solution so as to form an organic mixture.

6. The method of claim 5, further comprising thereafter adding the organic mixture to an aqueous solution so as to form a suspension polymerization mixture.

7. The method of claim 6, further comprising subjecting the suspension polymerization mixture to an elevated temperature in a range from 60 to 90 degrees Celsius.

8. The method of claim 7, wherein the suspension polymerization mixture is subjected to the elevated temperature for a period in a range from 4 to 20 hours.

9. The method of claim 1, wherein the polymer is formed by attaching to the prepolymer at least one amino group selected from the group consisting of a secondary amino group, a tertiary amino group and a quaternary amino group as the anion exchanging group.

10. The method of claim 1, wherein the polymer is formed by attaching to the prepolymer a tertiary amino group as the anion exchanging group.

11. The method of claim 1, wherein the polymer is formed by attaching to the prepolymer a morpholino group or a diethylamino group as the anion exchanging group.

12. The method of claim 1, wherein the perfluoro compound is has as the acidic group at the terminal, a sulfo group, a carboxyl group, or a hydroxyl group.

13. The method of claim 1, wherein the polymer has an average particle size in a range from 10 to 100 microns.

14. The method of claim 1, wherein the polymer is used as a filler in a preprocessing column that measures the perfluoro compound.

15. The method of claim 1, wherein the anion exchanging group has an ammonium group represented by formula [3]:

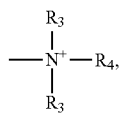

[3]

wherein each of $R_3$ represents independently a linear alkyl group having from 1 to 3 carbon atoms, and $R_4$ represents a linear alkyl group having from 1 to 6 carbon atoms.

16. A method of measuring drugs, comprising steps of:
contacting at least one drug with a polymer,
wherein the polymer includes a prepolymer having an anion exchange group attached to a gycidyl group of the prepolymer,
the prepolymer is a polymerization product of a compound of formula [1]:

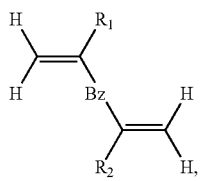

[1]

wherein each of $R_1$ and $R_2$ independently represents a hydrogen atom, a linear alkyl group having from 1 to 3 carbon atoms or a halogen atom, and Bz represents benzene ring,
a compound of formula [2]:

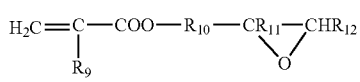

[2]

wherein $R_9$ represents a hydrogen atom, a linear alkyl group having from 1 to 3 carbon atoms or a halogen atom, $R_{10}$ represents a linear alkylene group having from 1 to 3 carbon atoms, and each of $R_{11}$ and $R_{12}$ independently represents a hydrogen atom or a linear alkyl group having from 1 to 6 carbon atoms, and further
a compound of formula [4]:

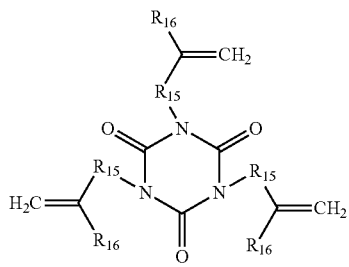

[4]

wherein each of three $R_{15}$ represents independently a linear alkylene group having from 1 to 3 carbon atoms, each of three $R_{16}$ independently represents a hydrogen atom, and a linear alkyl group having from 1 to 3 carbon atoms or a halogen atom, and the anion exchanging group has an ammonium group represented by formula [3]:

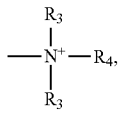
[3]

wherein each of $R_3$ represents independently a linear alkyl group having from 1 to 3 carbon atoms, and $R_4$ represents a linear alkyl group having from 1 to 6 carbon atoms; and measuring the at least one drug.

17. The method of claim 16,
wherein a molar ratio of the compound of the formula [1], the compound of the formula [2], and the compound of the formula [4] is in ranges from 60 to 85 : from 14 to 30: from 1 to 10, respectively.

18. A method of measuring a perfluoro compound having an acidic group at terminal, comprising steps of:
contacting the perfluoro compound with a polymer,
wherein the polymer consists of a prepolymer having an anion exchange group attached to a gycidyl group of the prepolymer,
the prepolymer is a polymerization product of a compound of formula [1]:

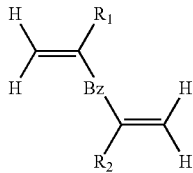
[1]

wherein each of $R_1$ and $R_2$ independently represents a hydrogen atom, a linear alkyl group having from 1 to 3 carbon atoms, or a halogen atom, and Bz represents benzene ring, and a compound of formula [2]:

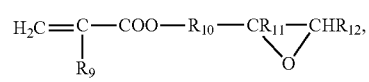
[2]

wherein $R_9$ represents a hydrogen atom, a linear alkyl group having from 1 to 3 carbon atoms or a halogen atom, $R_{10}$ represents a linear alkylene group having from 1 to 3 carbon atoms, and each of $R_{11}$ and $R_{12}$ independently represents a hydrogen atom or a linear alkyl group having from 1 to 6 carbon atoms, and a molar ratio of the compound of the formula [1]/ the compound of the formula [2] is in a range from 60/40 to 90/10 ;

contacting at least a portion the perfluoro compound with a washing solution having a pH of 8 or less;

eluting at least a portion of the perfluoro compound with an eluting solution having a pH in a range from 8 to 14;

subjecting an eluted portion of the perfluoro compound to mass spectrometry; and measuring the perfluoro compound.

19. The method of claim 18, wherein the prepolymer is formed by steps comprising:
a) mixing the compound of the formula [1] with the compound of the formula [2] in a non-aqueous, organic solution so as to form an organic mixture;
b) adding the organic mixture to an aqueous solution so as to form a suspension polymerization mixture; and
c) subjecting the suspension polymerization mixture to an elevated temperature in a range from 60 to 90 degrees Celsius for a period in a range from 4 to 20 hours.

* * * * *